United States Patent
Lee et al.

(10) Patent No.: US 10,729,912 B2
(45) Date of Patent: Aug. 4, 2020

(54) INSERTABLE PHOTOELECTRIC DEVICE USING ABSORPTION OF LIGHT PENETRATING SKIN AND ELECTRONIC APPARATUS HAVING SAME PHOTOELECTRIC DEVICE

(71) Applicant: GWANGJU INSTITUTE OF SCIENCE AND TECHNOLOGY, Gwangju (KR)

(72) Inventors: Jongho Lee, Gwangju (KR); Kwangsun Song, Gwangju (KR); Yong Chul Kim, Gwangju (KR); Jung Hyun Han, Gwangju (KR)

(73) Assignee: GWANGJU INSTITUTE OF SCIENCE AND TECHNOLOGY, Buk-gu, Gwangju (KR)

( * ) Notice: Subject to any disclaimer, the term of this patent is extended or adjusted under 35 U.S.C. 154(b) by 168 days.

(21) Appl. No.: 15/579,824

(22) PCT Filed: Jun. 2, 2016

(86) PCT No.: PCT/KR2016/005858
§ 371 (c)(1),
(2) Date: Dec. 5, 2017

(87) PCT Pub. No.: WO2016/195397
PCT Pub. Date: Dec. 8, 2016

(65) Prior Publication Data
US 2018/0154158 A1    Jun. 7, 2018

(30) Foreign Application Priority Data
Jun. 5, 2015 (KR) .................. 10-2015-0079667

(51) Int. Cl.
*A61N 1/378* (2006.01)
*H01L 31/048* (2014.01)
(Continued)

(52) U.S. Cl.
CPC .......... *A61N 1/378* (2013.01); *A61N 1/3787* (2013.01); *H01L 31/02* (2013.01); *H01L 31/04* (2013.01);
(Continued)

(58) Field of Classification Search
CPC .... A61N 1/378; A61N 1/3975; H01L 31/042; H01L 31/043; H01L 31/048
(Continued)

(56) References Cited

U.S. PATENT DOCUMENTS 6,323,416 B1 * 11/2001 Komori ................. B32B 17/04
                                                    136/259
6,961,619 B2 * 11/2005 Casey ................. A61N 1/3787
                                                    607/33
(Continued)

FOREIGN PATENT DOCUMENTS

JP    2000079170 A    3/2000
KR    1020100095755 A    1/2010
(Continued)

OTHER PUBLICATIONS

International Search Report for Application No. PCT/KR2016/005858, dated Oct. 21, 2016, 3 Pages.
(Continued)

*Primary Examiner* — Chrstopher A Flory
(74) *Attorney, Agent, or Firm* — Brooks Kushman P.C.

(57) ABSTRACT

An implantable photovoltaic device. The implantable photovoltaic device includes: at least two solar microcells configured to absorb sunlight; a thin film wire configured to connecting the at least two solar microcells to each other; a film configured to support the solar microcells; an upper encapsulation layer configured to encapsulate an upper side of the solar microcells and shield the solar microcells from the outside; and a lower encapsulation layer configured to
(Continued)

US 10,729,912 B2

Page 2 encapsulate a lower side of the film and connect to the encapsulation layer. According to the idea of the present invention, it is possible to obtain a photovoltaic device which stably and harmlessly operates in a living body.

16 Claims, 19 Drawing Sheets

(51) Int. Cl.
  H02S 40/38    (2014.01)
  H01L 31/02    (2006.01)
  H01L 31/04    (2014.01)
  H01L 31/05    (2014.01)
  H01L 31/043   (2014.01)

(52) U.S. Cl.
  CPC .......... *H01L 31/043* (2014.12); *H01L 31/048* (2013.01); *H01L 31/0481* (2013.01); *H01L 31/0508* (2013.01); *H01L 31/0512* (2013.01); *H02S 40/38* (2014.12)

(58) Field of Classification Search
  USPC .......................................................... 607/61
  See application file for complete search history.

(56) References Cited

U.S. PATENT DOCUMENTS

| | | | | |
|---|---|---|---|---|
| 7,003,353 | B1* | 2/2006 | Parkhouse | A42B 1/242 320/108 |
| 10,285,590 | B2* | 5/2019 | Blaauw | A61B 3/16 |
| 2001/0054437 | A1* | 12/2001 | Komori | B32B 17/04 136/259 |
| 2005/0004619 | A1* | 1/2005 | Wahlstrand | A61N 1/3787 607/45 |
| 2006/0085051 | A1 | 4/2006 | Fritsch | |
| 2007/0112263 | A1* | 5/2007 | Fink | A61B 3/16 600/398 |
| 2008/0219320 | A1* | 9/2008 | Liu | G01K 7/22 374/185 |
| 2009/0326597 | A1* | 12/2009 | Zommer | A61N 1/3787 607/5 |
| 2010/0217351 | A1 | 8/2010 | Choe et al. | |
| 2010/0249890 | A1 | 9/2010 | Choi et al. | |
| 2011/0212304 | A1* | 9/2011 | Han | H05B 33/04 428/172 |
| 2011/0266561 | A1* | 11/2011 | Rogers | H01L 27/14643 257/88 |
| 2012/0145240 | A1* | 6/2012 | Carcia | B32B 17/10018 136/258 |
| 2012/0245444 | A1* | 9/2012 | Otis | A61B 5/1486 600/345 |
| 2013/0041235 | A1* | 2/2013 | Rogers | A61B 5/6867 600/306 |
| 2014/0093700 | A1* | 4/2014 | Han | H05B 33/04 428/172 |
| 2014/0144480 | A1 | 5/2014 | Lee | |
| 2014/0220422 | A1* | 8/2014 | Rogers | H01L 23/08 429/163 |
| 2014/0330337 | A1* | 11/2014 | Linke | A61N 1/3787 607/45 |
| 2014/0373898 | A1* | 12/2014 | Rogers | H01L 27/14643 136/246 |
| 2015/0100110 | A1* | 4/2015 | Towe | A61N 1/3787 607/61 |
| 2015/0280129 | A1* | 10/2015 | Kim | H01L 51/0097 257/40 |
| 2015/0373831 | A1* | 12/2015 | Rogers | H01L 23/22 429/121 |
| 2015/0380355 | A1* | 12/2015 | Rogers | H01L 23/5389 257/773 |
| 2016/0015987 | A1* | 1/2016 | Perraud | A61N 1/3787 607/61 |
| 2016/0082272 | A1* | 3/2016 | Karst | A61N 1/3787 607/61 |
| 2017/0179356 | A1* | 6/2017 | Rogers | H01L 27/14643 |
| 2018/0159037 | A1* | 6/2018 | McAlpine | H01L 51/0004 |

FOREIGN PATENT DOCUMENTS

| | | | |
|---|---|---|---|
| KR | 1020100107303 | A | 5/2010 |
| KR | 101051026 | B1 | 9/2010 |
| KR | 1020140078398 | A | 6/2014 |
| KR | 101404472 | B1 | 11/2014 |

OTHER PUBLICATIONS

Office Action for Korean Application No. 10-2016-0068654, dated Aug. 21, 2017, 5 Pages.
Notice of Allowance for Korean Application No. 10-2016-0068654, dated Nov. 30, 2017, 2 Pages.
Mond et al., "The 11th world survey of cardiac pacing and implantable cardioverter-defibrillators Calendar year 2009—A world society of Arrhythmia's project," PACE—Pacing Clin. Electrophysiol. 34, 10131027 (2011), 3 Pages.
Wood et al., "Cardiac pacemakers from the patient's perspective," Circulation 105, 21362138 (2002), 7 Pages.
Kurtz et al., "Implantation trends and patient profiles for pacemakers and implantable cardioverter defibrillators in the United States: 1993-2006," PACE—Pacing Clin. Electrophysiol. 33, 705711 (2010), 1 Page.
Potkay, J. A., "Long term, implantable blood pressure monitoring systems," Biomed. Microdevices 10, 379392 (2008), 12 Pages.
Henry, C., "Getting under the skin: implantable glucose sensors," Anal. Chem. 70, 594A598A (1998), 1 Page.
Chow et al., "The artificial silicon retina microchip for the treatment of vision loss from retinitis pigmentosa," Arch. Ophthalmol. 122, 460469 (2004), 2 Pages.
Someya et al., "A large-area, flexible pressure sensor matrix with organic field-effect transistors for artificial skin applications," Proc. Natl. Acad. Sci. U. S. A. 101, 99669970 (2004), 7 Pages.
Wang et al., "User-interactive electronic skin for instantaneous pressure visualization," Nat. Mater. 12, 16 (2013), 1 Page.
Minev et al., "Electronic dura mater for long-term multimodal neural interfaces," Science 347, 159163 (2012), 65 Pages.
Goshen et al., "Dynamics of retrieval strategies for remote memories," Cell 147, 678689 (2011), 7 Pages.
Kim et al., "Injectable, Cellular-Scale Optoelectronics with Applications for Wireless Optogenetics," Science 340, 211216 (2013), 7 Pages.
Zebda et al., "Mediatorless high-power glucose biofuel cells based on compressed carbon nanotube-enzyme electrodes," Nat. Commun. 2, 370 (2011), 21 Pages.
Halámková et al., "Implanted biofuel cell operating in a living snail," J. Am. Chem. Soc. 134, 50405043 (2012), 1 Page.
Wang et al., "Piezoelectric nanogenerators based on zinc oxide nanowire arrays," Science 312, 242246 (2006), 6 Pages.
Hwang et al., "Self-powered cardiac pacemaker enabled by flexible single crystalline PMN-PT piezoelectric energy harvester," Adv. Mater. 26, 48804887 (2014), 3 Pages.
Dagdeviren et al., "Conformal piezoelectric energy harvesting and storage from motions of the heart, lung, and diaphragm," Proc. Natl. Acad. Sci. U. S. A. 111, 192732 (2014), 10 Pages.
Mercier, et al., "Energy extraction from the biologic battery in the inner ear," Nat. Biotechnol. 30, 12403 (2012), 7 Pages.
Nemani et al., "In vitro and in vivo evaluation of SU-8 biocompatibility," Mater. Sci. Eng. C 33, 44534459 (2013), 9 Pages.
Norland Products, "Norland UV adhesive," https://www.norlandprod.com/UV-news.asp, 3 Pages.
Bélanger et al., "Hemocompatibility, biocompatibility, inflammatory and in vivo studies of primary reference materials low-density polyethylene and polydimethylsiloxane: A review," J. Biomed. Mater. Res. 58, 467477 (2001), 2 Pages.
Ming et al., "PTEN Positively Regulates UVB-induced DNA Damage Repair," Cancer Res., Aug. 1, 2011, 71 (15), 5287-5295, 10 Pages.

(56) References Cited

OTHER PUBLICATIONS

Benavides et al., "The hairless mouse in skin research," J. Dermatol. Sci. 53, 1018 (2009), 19 Pages.
Lakshmanan, et al., "Infection rate of percutaneous Kirschner wire fixation for distal radius fractures," J. Orthop. Surg. (Hong Kong) 18, 8586 (2010), 2 Pages.
Niv et al., "Overcoming the bandgap limitation on solar cell materials," Appl. Phys. Lett. 100, 14 (2012), 4 Pages.
Anderson et al., "Foreign body reaction to biomaterials," Semin. Immunol. 20, 86100 (2008), 22 Pages.
Bernerd et al., "Evaluation of the protective effect of sunscreens on in vitro reconstructed human skin exposed to UVB or UVA irradiation," Photochem. Photobiol. 71, 314320 (2000), 3 Pages.
Lodge, Jr., J. "Air quality guidelines for Europe," Environ. Sci. Pollut. Res. 3, 23 (1996), 1 Page.
World Health Organization(WHO). Guidelines for drinking-water quality 4th ed. (2011), 564 Pages.
Valøen et al., "The effect of PHEV and HEV duty cycles on battery and battery pack performance," Plug-in hybrid Veh. Conf. 19 (2007), 9 Pages.
Lee et al., "Stretchable semiconductor technologies with high areal coverages and strain-limiting behavior: Demonstration in high-efficiency dual-junction GaInP/Gatis photovoltaics," Small 8, 18511856 (2012), 7 Pages.
Park et al., "Immunologic and tissue encapsulation of flexible/stretchable electronics and optoelectronics," Adv. Healthc. Mater. 3, 515525 (2014), 11 Pages.
Bird et al., "Bird simple spectral model," National Renewable Energy Laboratory (NREL), http://rredc.nrel.gov/solar/models/spectral/, 2 Pages.
Yakovlev et al., "Implantable biomedical devices: Wireless powering and communication," IEEE Commun. Mag. 50, 152-159 (2012), 8 Pages.
Ramrakhyani et al., "Design and optimization of resonance-based efficient wireless power delivery systems for biomedical implants," IEEE Trans. Biomed. Circuits Syst. 5, 48-63 (2011), 4 Pages.
Si et al., "A frequency control method for regulating wireless power to implantable devices," Biomed. circuits Syst. 2, 22-29 (2008), 3 Pages.
Ho et al., "Wireless power transfer to deep-tissue microimplants," Proc. Natl. Acad. Sci. 111, 7974-7979 (2014), 10 Pages.
Kwangsun Song et al., "Subdermal Flexible Solar Cell Arrays for Powering Medical Electronic Implants," Advanced Healthcare Materials, May 2016, pp. 1572-1580, 9 Pages.
Korean Office Action.
Korean Notice of Allowance.
International Search Report.
KR1020140078398A, English Abstract.
KR1020100107303A, English Abstract and U.S. Equivalent U.S. Pub. No. 2010/0249890.
KR1020100095755A; KR101051026B1, English Abstract and U.S. Equivalent U.S. Pub. No. 2010/0217351.
KR101404472B1, English Abstract and U.S. Equivalent U.S. Pub. No. 2014/01444480.
JP2000079170A, English Abstract.

\* cited by examiner

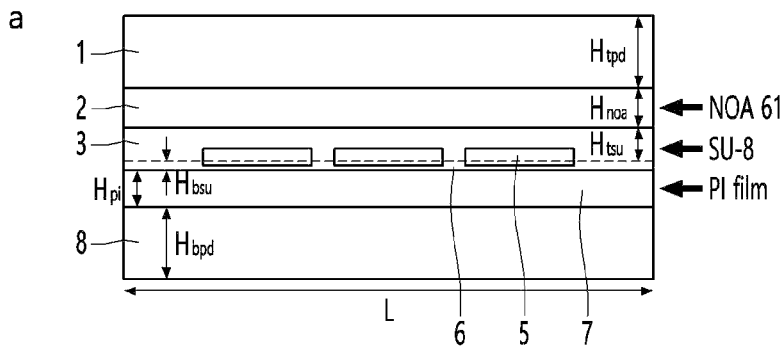

b $E_{su} = 2$ Gpa, $E_{pi} = 3.2$ Gpa $E_{noa} =$ Gpa, $E_{pd} = 2$ Mpa $H_{pi} = 12.5$ μm, $H_{tpd} = H_{bpd} = 100$ μm, $H_{tsu} = 10$ μm, $H_{bsu} = 2$ μm, $H_{noa} = 23$ μm $L = 7.5$ mm, $L_{pi} = E_{pi}/E_{pd} \times L$, $L_{su} = E_{su}/E_{pd} \times L$, $L_{noa} = E_{noa}/E_{pd} \times L$ $S_1 = H_{bpd}/2$, $S_2 = H_{pd} + H_{pi}/2$, $S_3 = H_{pd} + H_{pi} + (H_{bsu} + H_{tsu})/2$ $S_4 = H_{pd} + H_{pi} + H_{bsu} + H_{tsu} + H_{noa}/2$ $S_5 = H_{pd} + H_{pi} + H_{bsu} + H_{tsu} + H_{noa} + H_{tpd}/2$ $A_1 = L \times H_{tpd}$, $A_2 = L_{pi} \times H_{pi}$, $A_3 = L_{su} \times H_{su}$, $A_4 = L_{noa} \times H_{noa}$, $A_5 = L_{tpd} \times H_{tpd}$ $S_{neutral\ plane} = \sum S_i A_i / \sum A_i$, $S_{neutral\ plane}$
$= (S_1 A_1 + S_2 A_2 + S_3 A_3 + S_4 A_4 + S_5 A_5)/(A_1 + A_2 + A_3 + A_4 + A_5)$ $S_{neutral\ plane} \approx 117.5$ μm (center of microcells)

Fig. 6

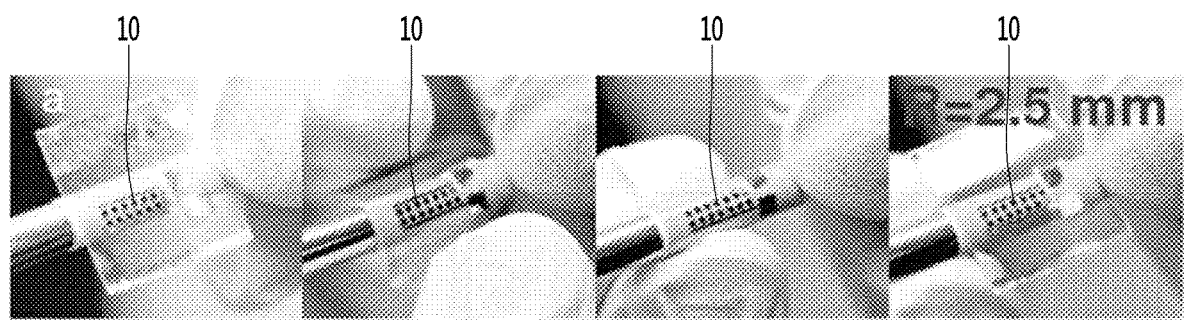
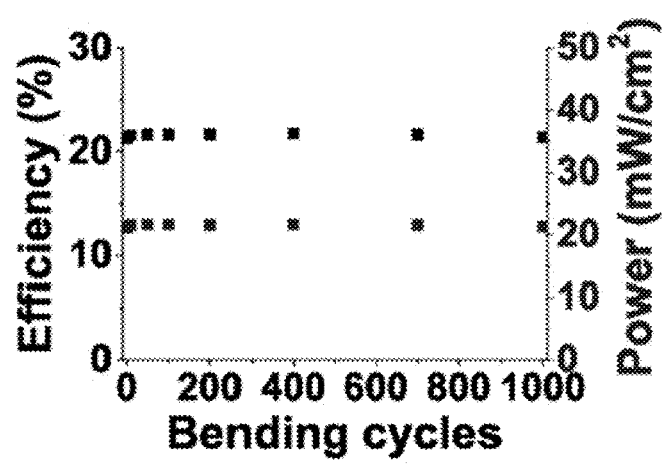
Fig. 9

(1) Light source
(2) Reflectance detector
(3) Transmittance detector
(4) Mouse skin $$J_{im,GaInP} = q\int_{400}^{900} T(\lambda)\Phi(\lambda)EQE(\lambda)d\lambda$$
$$= 5q\sum_{n=0}^{99} T(400+5n)\Phi(400+5n)EQE(400+5n)$$
$$J_{im,GaAs} = q\int_{400}^{900} T(\lambda)\Phi(\lambda)EQE(\lambda)d\lambda$$
$$= 5q\sum_{n=0}^{99} T(400+5n)\Phi(400+5n)EQE(400+5n)$$
$$J_{implant} = \min(J_{im,GaInP}, J_{im,GaAs}) = J_{im,GaInP}$$

q = elementary charge[C] = $1.60217657 \times 10^{-19}$ C

T = Transmittance of skin $\Phi$ = Photon flux[$cm^{-2}\ s^{-1}nm^{-1}$]

EQE = External quntum efficiency

J = Current density[$mA/cm^2$]

Fig. 14

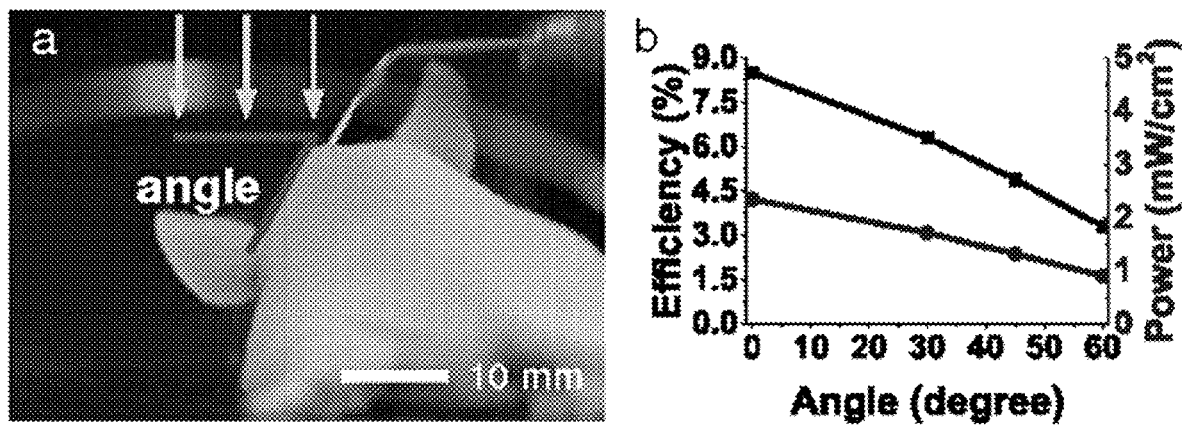

Fig. 15 a a

Charging a pacemaker battery with the IPVs

Implantable photovoltaics
- Conversion efficiency : 8.2%
- Current : 160 μA

Pacemaker: Adapta ADDRS1, Medtronics
- Capacity : 830 mAh (Sigma 213 lithium-iodine)
- Longevity : 8 years (DDDR or DDD 50% mode)
- Rate and pulse width: 60 ppm, 0.4 ms
- Lead impedance: 1000 Ω
- Charging efficiency : 85%

Daily power consumption
= 830 mAh/(8×365 day) = 0.28425 mAh/day
Charging time for power consumption
= 0.28425 mAh/(0.16 mA×0.85) ≈ 2 hr 6 min

Fig. 21

| Additional layer | Ingredients | Volume or thickness | Efficiency |
|---|---|---|---|
| Sunscreen | bis-ethylhexyloxyphenol methoxyphenyltriazine, titanium dioxide, ethylhexylmethoxycinnamate, etc. | ~9 mg/cm$^2$ | 7.5% |
| Moisturizer | glycerin, butylene glycol, dipropylene glycol, etc. | ~13 mg/cm$^2$ | 7.8% |
| Cheek-and-lip stain | ethylhexyl stearate, butylene glycol, pentylene glycol, etc. | ~5 mg/cm$^2$ | 6.1% |
| Hydrocolloid bandage | carboxymethyl cellulose, pectin, gelatin, etc. | ~0.53 mm | 6.1% |

Fig. 22

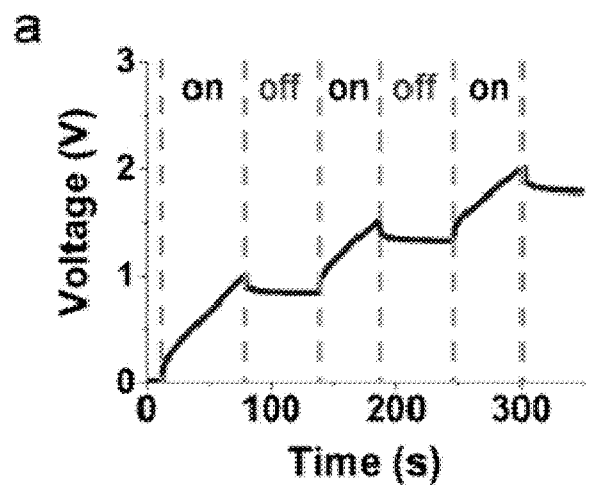
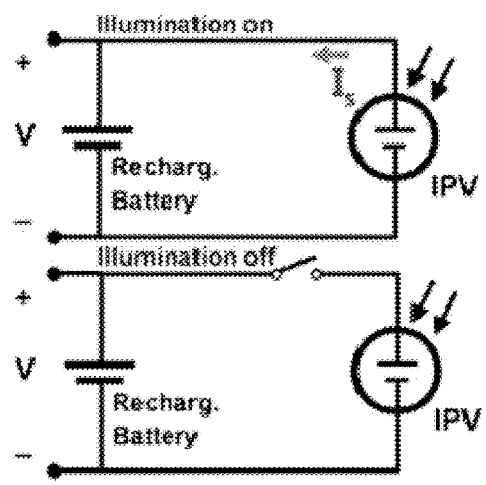
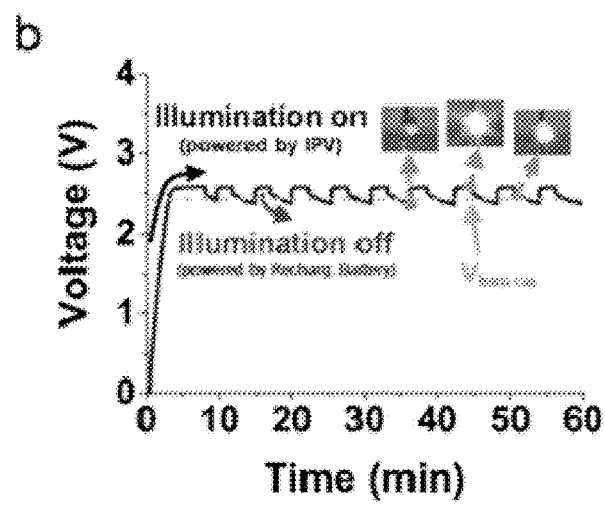
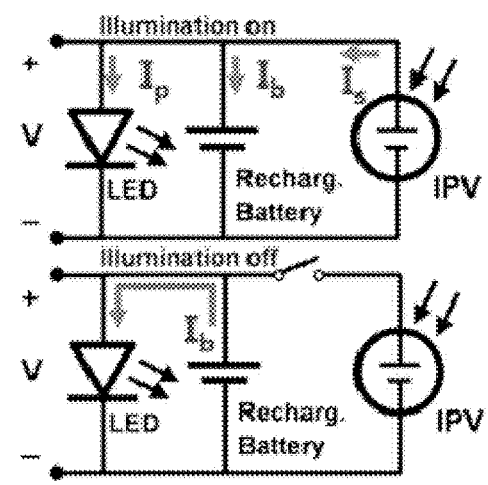
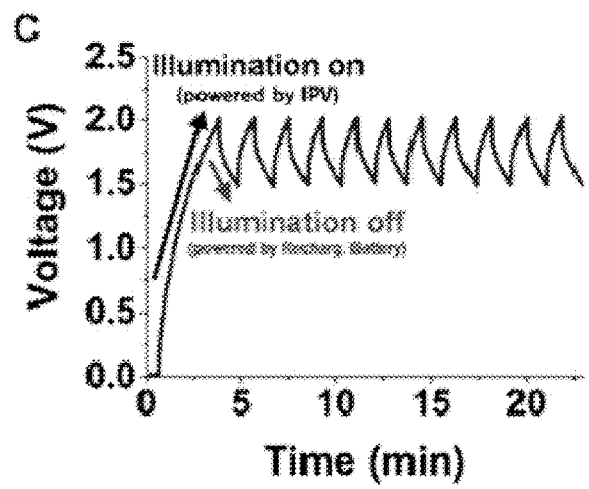
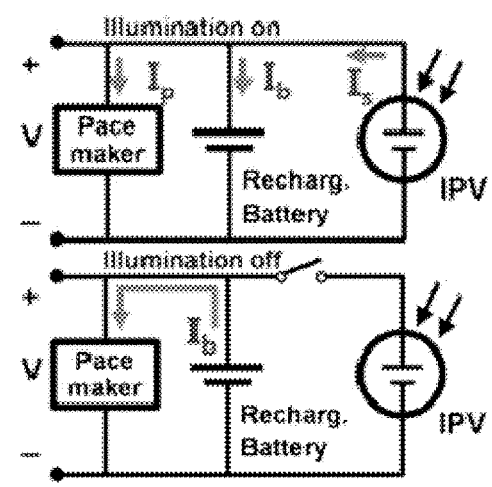
Fig. 24

INSERTABLE PHOTOELECTRIC DEVICE USING ABSORPTION OF LIGHT PENETRATING SKIN AND ELECTRONIC APPARATUS HAVING SAME PHOTOELECTRIC DEVICE

CROSS-REFERENCE TO RELATED APPLICATION

This application is the U.S. national phase of PCT Application No. PCT/KR2016/005858 filed on Jun. 02, 2016, which claims priority to KR Patent Application No. 10-2015-0079667 filed on Jun. 5, 2015, the disclosures of which are incorporated in their entirety by reference herein.

TECHNICAL FIELD

The present invention relates to an implantable photovoltaic device using absorption of light penetrating a skin, which can obtain a high level of energy within a living body without complicated medical treatment.

BACKGROUND ART

As the average lifespan of human increases, the use of devices for monitoring a biosignal in a human body and assisting organs with impaired functions is increasing. For example, there are insertable cardiac monitors (ICMs) or cardiac pacemakers for observing the heartbeat of the heart, and human implantable medical devices such as spinal cord stimulators, vagus nerve stimulators, and deep brain stimulators.

As such, the increase in the demand of various human implantable medical devices promotes the development of new types of human implantable medical devices, such as blood pressure monitors (Non-Patent Document 4), glucose monitors (Non-Patent Document 5), artificial retinas (Non-Patent Document 6), and related studies (Non-Patent Documents 7-11).

All the implantable medical devices require power so as to operate within the body. However, since such devices currently use a battery having a limited capacity as a power source, periodic re-operation is required to replace the depleted battery. For example, a battery of a pacemaker can be usually used for 5 to 8 years, and repeated re-operations are required to replace the battery (Non-Patent Document 2).

In order to solve the problem that must periodically re-operate so as to replace the battery of the human implantable medical device, research has recently been conducted into in vivo power production technologies using electrochemical reactions (Non-Patent Documents 12 and 13), piezoelectric effect (Non-Patent Documents 14-16), wireless power transmission (Non-Patent Documents 32-35), and various application technologies (Non-Patent Document 17). However, the in vivo power production method is expected t require significant improvement so as to overcome the limitations such as the amount of power produced, blood compatibility, durability, and necessity of thoracic surgery.

The following Non-Patent Documents are provided for reference in order to help understanding of the present invention.

1. Mond, H. G. & Proclemer, A. The 11th world survey of cardiac pacing and implantable cardioverter-defibrillators: Calendar year 2009—A world society of Arrhythmia's project. PACE—Pacing Clin. Electrophysiol. 34, 10131027 (2011).

2. Wood, M. a. & Ellenbogen, K. a. Cardiac pacemakers from the patient's perspective. Circulation 105, 21362138 (2002).

3. Kurtz, S. M. et al. Implantation trends and patient profiles for pacemakers and implantable cardioverter defibrillators in the United States: 1993-2006. PACE—Pacing Clin. Electrophysiol. 33, 705711 (2010).

4. Potkay, J. A. Long term, implantable blood pressure monitoring systems. Biomed. Microdevices 10, 379392 (2008).

5. Henry, C. Getting under the skin: implantable glucose sensors. Anal. Chem. 70, 594A598A (1998).

6. Chow, A. Y. et al. The artificial silicon retina microchip for the treatment of vision loss from retinitis pigmentosa. Arch. Ophthalmol. 122, 460469 (2004).

7. Someya, T. et al. A large-area, flexible pressure sensor matrix with organic field-effect transistors for artificial skin applications. Proc. Natl. Acad. Sci. U.S.A. 101, 99669970 (2004).

8. Wang, C. et al. User-interactive electronic skin for instantaneous pressure visualization. Nat. Mater. 12, 16 (2013).

9. Minev, I. R. et al. Electronic dura mater for long-term multimodal neural interfaces. Science 347, 159163 (2012).

10. Goshen, I. et al. Dynamics of retrieval strategies for remote memories. Cell 147, 678689 (2011).

11. Kim, T. et al. Injectable, Cellular-Scale Optoelectronics with Applications for Wireless Optogenetics. Science 340, 211216 (2013).

12. Zebda, A. et al. Mediatorless high-power glucose biofuel cells based on compressed carbon nanotube-enzyme electrodes. Nat. Commun. 2, 370 (2011).

13. Halmkov, L. et al. Implanted biofuel cell operating in a living snail. J. Am. Chem. Soc. 134, 50405043 (2012).

14. Wang, Z. L. & Song, J. Piezoelectric nanogenerators based on zinc oxide nanowire arrays. Science 312, 242246 (2006).

15. Hwang, G. T. et al. Self-powered cardiac pacemaker enabled by flexible single crystalline PMN-PT piezoelectric energy harvester. Adv. Mater. 26, 48804887 (2014).

16. Dagdeviren, C. et al. Conformal piezoelectric energy harvesting and storage from motions of the heart, lung, and diaphragm. Proc. Natl. Acad. Sci. U.S.A. 111, 192732 (2014).

17. Mercier, P. P., Lysaght, A. C., Bandyopadhyay, S., Chandrakasan, A. P. & Stankovic, K. M. Energy extraction from the biologic battery in the inner ear. Nat. Biotechnol. 30, 12403 (2012).

18. Nemani, K. V., Moodie, K. L., Brennick, J. B., Su, A. & Gimi, B. In vitro and in vivo evaluation of SU-8 biocompatibility. Mater. Sci. Eng. C 33, 44534459 (2013).

19. Norland Products. Norland UV adhesive. https://www.norlandprod.com/UV-news.asp 20. Blanger, M. C. & Marois, Y. Hemocompatibility, biocompatibility, inflammatory and in vivo studies of primary reference materials low-density polyethylene and polydimethylsiloxane: A review. J. Biomed. Mater. Res. 58, 467477 (2001).

21. Benavides, F., Oberyszyn, T. M., VanBuskirk, A. M., Reeve, V. E. & Kusewitt, D. F. The hairless mouse in skin research. J. Dermatol. Sci. 53, 1018 (2009).

22. Lakshmanan, P., Dixit, V., Reed, M. R. & Sher, J. L. Infection rate of percutaneous Kirschner wire fixation for distal radius fractures. J. Orthop. Surg. (Hong Kong) 18, 8586 (2010).

23. Niv, a., Abrams, Z. R., Gharghi, M., Gladden, C. & Zhang, X. Overcoming the bandgap limitation on solar cell materials. Appl. Phys. Lett. 100, 14 (2012).

24. Anderson, J. M., Rodriguez, A. & Chang, D. T. Foreign body reaction to biomaterials. Semin. Immunol. 20, 86100 (2008).

25. Bernerd, F., Vioux, C. & Asselineau, D. Evaluation of the protective effect of sunscreens on in vitro reconstructed human skin exposed to UVB or UVA irradiation. Photochem. Photobiol. 71, 314320 (2000).

26. Lodgejr, J. Air quality guidelines for Europe. Environ. Sci. Pollut. Res. 3, 2323 (1996).

27. World Health Organization (WHO). Guidelines for drinking-water quality 4th ed. (2011).

28. Valen, L. O. & Shoesmith, M. I. The effect of PHEV and HEV duty cycles on battery and battery pack performance. Plug-in hybrid Veh. Conf. 19 (2007).

29. Lee, J. et al. Stretchable semiconductor technologies with high areal coverages and strain-limiting behavior: Demonstration in high-efficiency dual-junction GaInP/GaAs photovoltaics. Small 8, 18511856 (2012).

30. Park, G. et al. Immunologic and tissue encapsulation of flexible/stretchable electronics and optoelectronics. Adv. Healthc. Mater. 3, 515525 (2014).

31. National Renewable Energy Laboratory (NREL). Bird simple spectral model. http://rredc.nrel.gov/solar/models/spectral/.

32. Yakovlev, A., Kim, S. & Poon, A. Implantable biomedical devices: Wireless powering and communication. IEEE Commun. Mag. 50, 152-159 (2012).

33. A. K. Ramrakhyani, Mirabbasi, S., Chiao, M. & M, C. Design and optimization of resonance-based efficient wireless power delivery systems for biomedical implants. IEEE Trans. Biomed. Circuits Syst. 5, 48-63 (2011).

34. Ping Si, Hu, a P., Malpas, S. & Budgett, D. A frequency control method for regulating wireless power to implantable devices. Biomed. circuits Syst. 2, 22-29 (2008).

35. Ho, J. S. et al. Wireless power transfer to deep-tissue microimplants. Proc. Natl. Acad. Sci. 111, 7974-7979 (2014).

DISCLOSURE OF THE INVENTION

Technical Problem

The present invention is proposed under the background described above, and proposes a new method capable of obtaining a high level of energy within a living body without complicated medical treatment.

Technical Solution

An implantable photovoltaic device using absorption of light penetrating a skin, according to the present invention, includes: at least two solar microcells configured to absorb sunlight; a thin film wire configured to connecting the at least two solar microcells to each other; a film configured to support the solar microcells; an upper encapsulation layer configured to encapsulate an upper side of the solar microcells and shield the solar microcells from the outside; and a lower encapsulation layer configured to encapsulate a lower side of the film and connect to the encapsulation layer. According to the present invention, it is possible to obtain the photovoltaic device that operates and is harmless to the living body even when implanted into the living body.

An electronic apparatus according to the present invention includes: a photovoltaic device including at least two solar microcells configured to absorb sunlight, a thin film wire configured to connecting the at least two solar microcells to each other, a film configured to support the solar microcells, an upper encapsulation layer configured to encapsulate an upper side of the solar microcells and shield the solar microcells from the outside, and a lower encapsulation layer configured to encapsulate a lower side of the film and connect to the encapsulation layer; and a battery configured to charge electricity produced by the photovoltaic device. According to the present invention, the electronic device can be implanted into the living body and can stably supply energy to the device required in the living body.

Advantageous Effects

According to the present invention, it is possible to obtain an ultra-thin in vivo solar cell which captures transmitted light penetrating a skin to generate DC electricity in vivo. According to this, a high level of electric energy can be obtained under the skin without a complicated medical procedure. In addition, no additional rectification circuit is required.

Illustratively, when applied to a living mouse having few hairs, the implantable photovoltaic device produced DC current of about 647 W. This is significantly higher than the previously reported studies. In order to demonstrate that the power production of the photovoltaic device completely implanted under the skin is possible, the present invention proposes an implantable photovoltaic device into which an LED or a pacemaker capable of confirming the operation of the photovoltaic device, and a rechargeable battery is integrated.

According to the present invention, the photovoltaic device implanted under the skin of the mouse having few hairs directly produces electricity and supplies the electricity to the manufactured pacemaker and LED. According to the direct/indirect biocompatibility test, it can be confirmed that the influence of toxic substances on the surrounding tissues is very slight due to the encapsulation layer.

BRIEF DESCRIPTION OF THE DRAWINGS

FIGS. 1 to 7 are views showing the concept of an embodiment.

FIGS. 8 to 24 are views for describing auxiliary data for understanding of the embodiment.

MODE FOR CARRYING OUT THE INVENTION

Hereinafter, exemplary embodiments will be described in detail with reference to the accompanying drawings. However, the embodiments of the present invention are not limited to the following embodiments. Those skilled in the art, who understand the spirit of the present invention, can readily suggest other embodiments included within the scope of the same concept by adding, changing, and deleting elements, but it will be apparent to those skilled in the art that this is also included within the scope of the present invention.

Prior to describing the embodiments, the range to which the present invention can be applied and its significance will be described first.

A human implantable medical device that continuously monitors or assists an organ in a human body is an important device in extending or maintaining the human lifespan (Non-Patent Document 1). However, at the present time, there is a limit in the amount of energy that can be stored in a battery used for driving a human implantable medical device (the human implantable medical device includes any devices that is inserted into a living body and performs an automated operation requiring a predetermined amount of energy). Thus, periodic re-operation for replacing the depleted battery (Non-Patent Document 3) has serious limitations that cause a mental/physical/economic burden on a patient.

Under this background, the inventors presented a new approach to delivering sustainable electrical energy to the human implantable medical device disposed under a skin, without any connection through the skin.

Embodiments include a method of obtaining energy by using a flexible photovoltaic device inserted under a skin. This method can convert light passing through the skin into electricity. From an experiment using a mouse, the potential of this approach was demonstrated by obtaining 33-45% of current in the living body, as compared with an amount that can be obtained in a photovoltaic device outside the living body.

A pacemaker may be operated for 24 hours with a charging time of about 2 hours in the in the inventive vivo photovoltaic device. In addition, the photovoltaic device, which is easy to resize and can be completely inserted through a simple medical procedure can contribute to expanding the development of implantable electric devices having various functions, which have been by the absence of power production in the human body.

Figure 1:
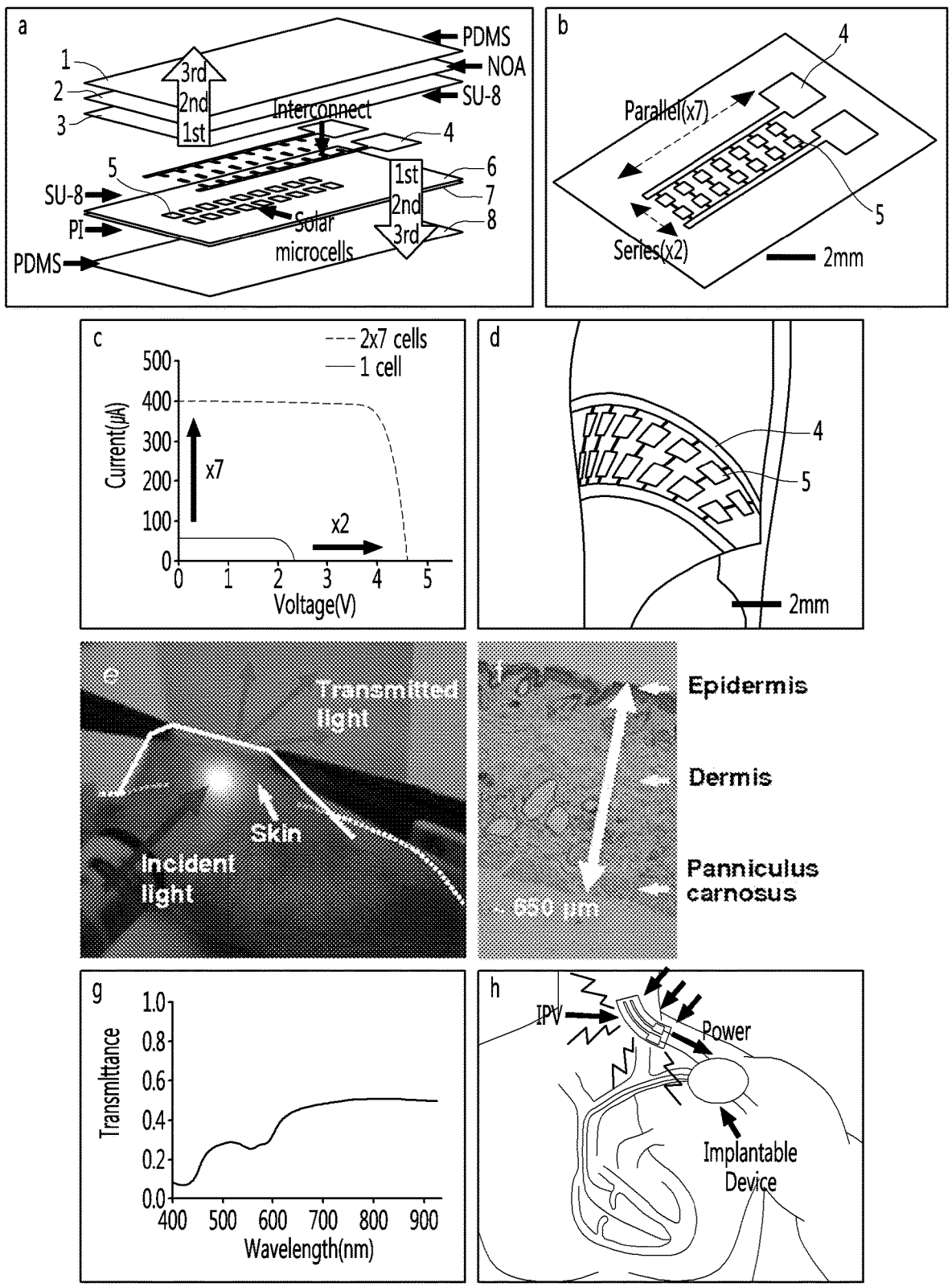

FIG. 1 is a view for describing a schematic configuration and operation of an implantable photovoltaic device.

FIG. 1*a* is an exploded perspective view showing the configuration the implantable photovoltaic device. Encapsulation layers (layers provided as 1, 2, 3, 6, 7, and 8) encapsulate solar microcells 5 and thin film wires 4 so as to prevent exchange of materials from the outside to the inside or from the inside to the outside. Therefore, even if inserted into the living body, a problem may not be caused. A thickness of the encapsulation layer is determined so as to minimize a deformation amount applied to a solar cell and a thin film wire.

More specifically, the sputtered thin film wires (Ti: 30 nm/Au: 300 nm) 4 may connect the ultra-thin dual-junction solar microcells 5 to each other. Here, the solar microcell 5 may have a size of 760 μm×760 μm and a thickness of 5.7 μm and may be made of GaInP/GaAs. The solar microcell 5 may be introduced into a polyimide (PI) film 7 made of a flexible material by a transfer-printed method. The PI may have a thickness of 12.5 μm.

The thin film wire 4 may be encapsulated by a multilayer film of a biocompatible and transparent polymer. As the multilayer film of the polymer, SU-8(3) (~2 μm, SU-8 2002), Norland optical adhesive (2) (~23 μm, NOA 61), and PDMS (1) (100-200 μm, Sylgard 184) (Non-Patent Documents 18-20) may be used. Such a simple design may provide a thin and flexible structure that is more mechanically suitable to the skin.

FIG. 1*b* shows a representative image of an unencapsulated implantable photovoltaic device including 14 solar microcells. The solar microcells 5 are arranged such that components of seven columns are connected in series and the seven columns are connected in parallel by using the thin film wires (Ti: 20 nm, Au: 300 nm) (not limited thereto). The number of microcells may be changed in various forms. Such a connection may improve a short-circuit current and an open-circuit voltage as shown in FIG. 1*c*.

FIG. 1*c* shows current-voltage characteristics of a solar microcell connected to a single solar microcell. The parallel/series-connected solar microcells increase the short circuit current seven times (Isc: 57 A→400 A) and increase the open circuit current twice (Voc: 2.3 V→4.6 V). A filling factor and conversion efficiency of the implantable photovoltaic device are 0.8 and 21.7%, respectively.

FIG. 1*d* shows an image of an implantable photovoltaic device that is in a flexibly bent state. The implantable photovoltaic device according to an embodiment is designed to minimize a strain applied to the thin film wires and the solar microcells which are brittle by the thickness adjustment of the encapsulation layers. Thus, there is no abnormality in the normal operation of the solar microcells 5 and the thin film wires 4 even if external deformation is applied.

The configuration of the thin film wire and the solar microcell will be described in more detail with reference to FIGS. 6 and 7.

Figure 8:
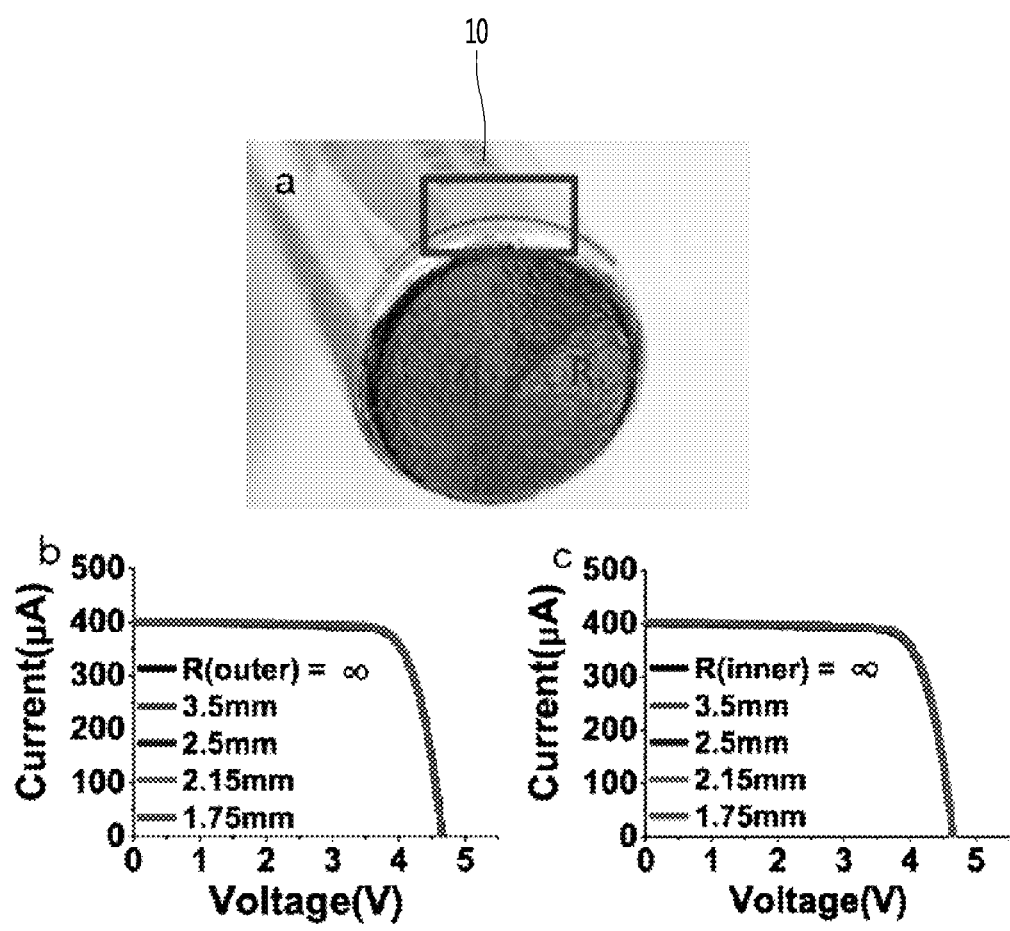

As shown in FIG. 8, it can be seen that the current-voltage characteristics of the implantable photovoltaic device are equally maintained even after the implantable photovoltaic device is bent at a radius of curvature of 1.75 mm.

As shown in FIG. 9, it can be seen that the conversion efficiency and power density are equally maintained even after 1,000 repetitive bending tests at a radius of curvature of 2.5 mm.

FIG. 1*e* demonstrates transmission properties of a skin by showing a light source (~532 nm) incident on two layers of a skin of a living mouse (SKH1-Hrhr) having few hairs, which is widely used in skin research as a substitute for a human skin, and transmitted light.

The transmitted light may be irradiated onto a white paper on the other side of the skin.

Table 2 presents a relevant mathematical modeling.

TABLE 2

$$J_{im,GaInP} = q \int_{400}^{900} T(\lambda)\Phi(\lambda)EQE(\lambda)d\lambda =$$

$$5q \sum_{n=n}^{99} T(400 + 5n)\Phi(400 + 5n)EQE(400 + 5n)$$

$$J_{im,GaAs} = q \int_{400}^{900} T(\lambda)\Phi(\lambda)EQE(\lambda)d\lambda =$$

$$5q \sum_{n=o}^{99} T(400 + 5n)\Phi(400 + 5n)EQE(400 + 5n)$$

$$J_{implant} = \min(J_{im,GaInP}, J_{im,GaAs}) = J_{im,gaInP}$$

q = elementaty charge[C] = 1.60217657 × 10$^{-19}$ C
T = Transmittence of skin
Φ = Photon flux[cm$^{-2}$ s$^{-1}$ nm$^{-1}$]
EQE = External quntum efficiency
J = Current density[mA/cm$^2$]

Table 2 represents a mathematical modeling for calculating current densities generated in GaInP of an upper layer and a GaAs structure of a lower layer, based on the transmittance measured using the skin of the SKH1-Hr mouse based on a solar radiation spectrum (see Non-Patent Document 31) and external quantum efficiency (EQE) (see Non-Patent Document 29) of a GaInP/GaAs dual-junction solar cell. The mathematical modeling provides a concrete method of values calculated by the following equations.

The observation of the light transmittance property of the skin has confirmed that light can be used as a medium for transmitting energy through the skin, as a power source for a variety of bio-implantable medical device, without being supplied with power through a wire inserted into a body, which may act as an infection route of a bacteria causing a disease (Non-Patent Document 22).

FIG. 1f shows a skin tissue image obtained by observing a skin (epidermis 50 μm, dermis 500 μm, panniculus carnosus 100 μm) with a microscope. In the case of the embodiment, the implantable photovoltaic device of the embodiment is inserted below the panniculus carnosus. Since the actual human skin consists of epidermis, dermis, and hypodermis, the implantable photovoltaic device may be inserted below the dermis.

Figure 10:
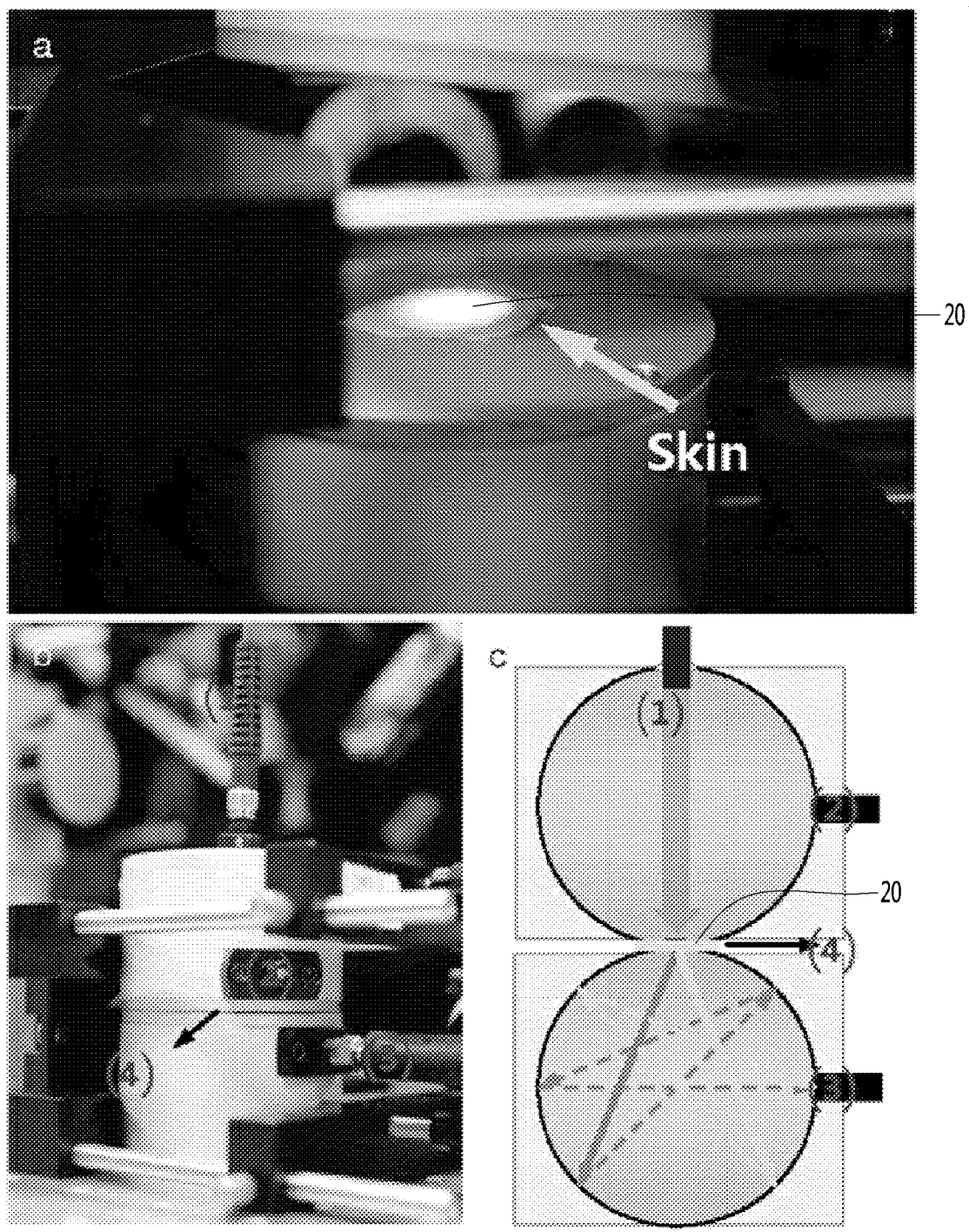

FIG. 1g shows a transmittance average measured within 10 minutes in 28 skin samples separated from seven mice. It was confirmed that the incident light had a transmittance of about 20-40% at a wavelength of 450-600 nm and a transmittance of about 50-60% at a wavelength of 600-950 nm. The transmittance measurement method can be confirmed through a transmittance test device of FIG. 10. As shown in FIG. 10c, it can be confirmed that the amount of light (3) transmitted through the skin 20 from the incident light (1).

Thus, the implantable photovoltaic device placed under the skin may absorb the light transmitted to the skin and continuously produce electricity.

FIG. 1h is a schematic view showing the application of the implantable photovoltaic device and can illustrate a photovoltaic device (IPV) that drives an implantable device such as a pacemaker. In the drawing, the implantable photovoltaic device (IPV) is disposed at a neck exposed to the outside and is bent. The implantable photovoltaic device exposed to the neck may supply power produced using the transmitted light and supply the power to the pacemaker.

Figure 2:
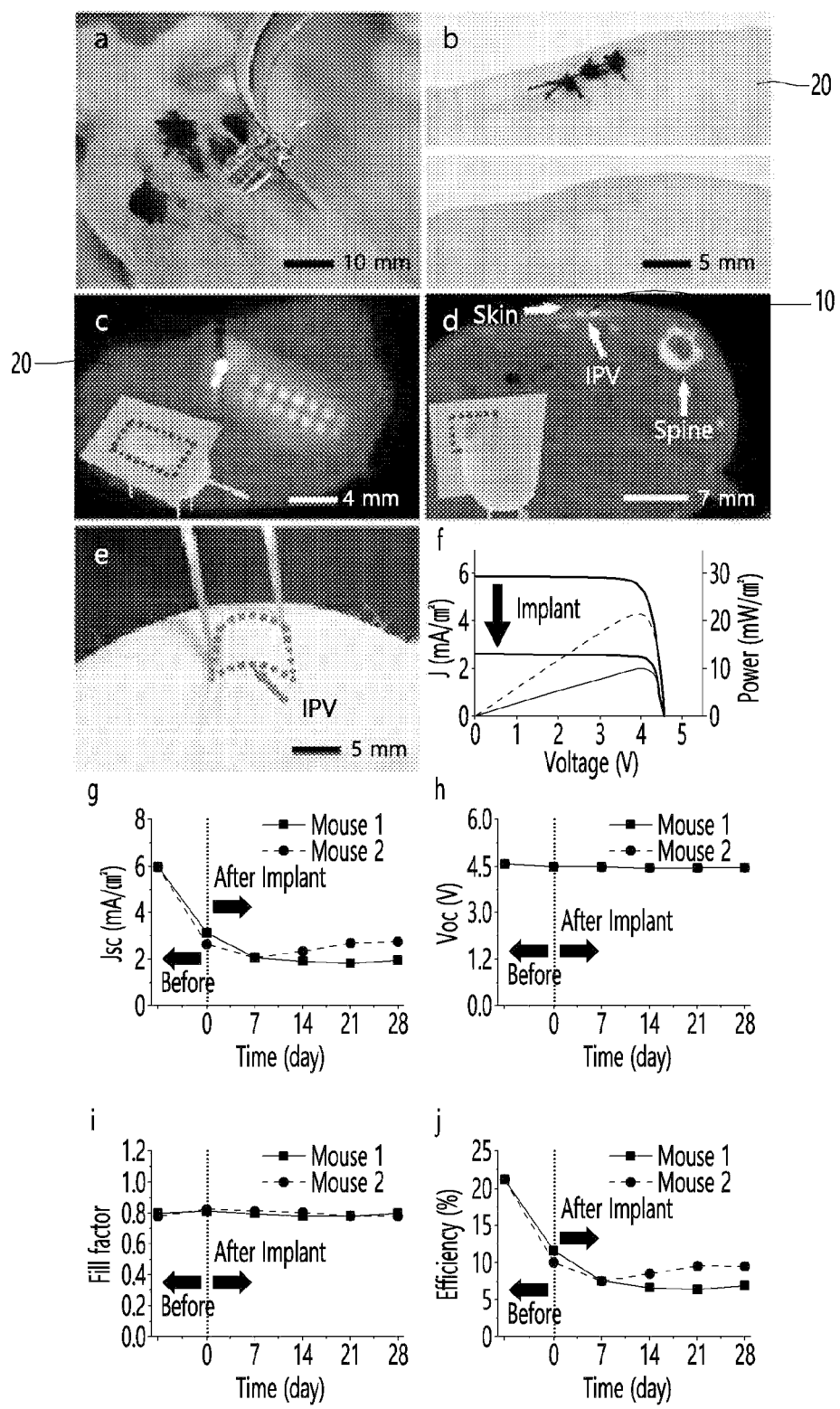

FIG. 2 shows the surgical procedure of implanting the implantable photovoltaic device and the electrical performance in the living body.

Figure 11:
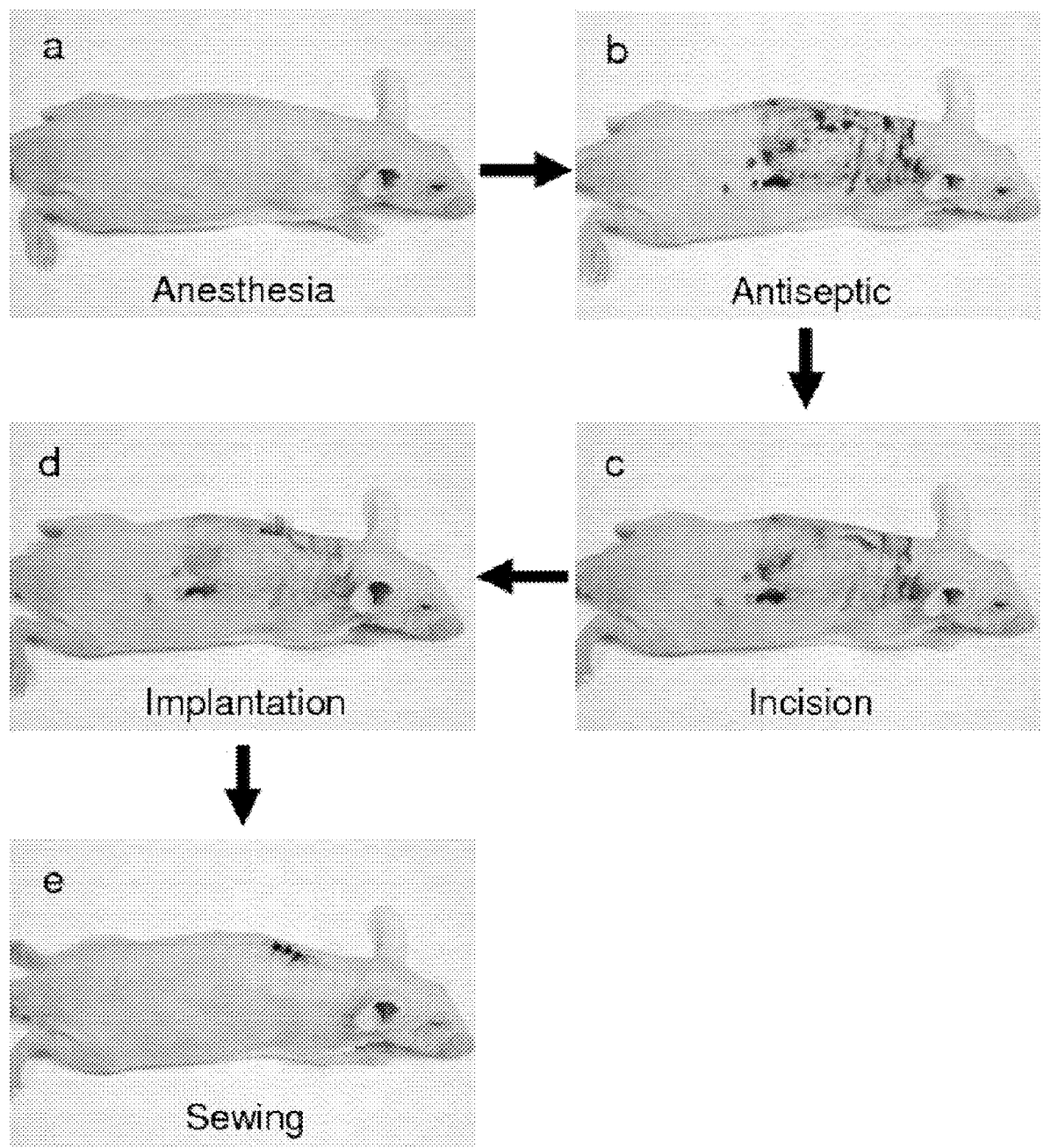

FIG. 2a shows a simple procedure image in which the implantable photovoltaic device is implanted under a skin of a mouse having few hairs. After the implant, a copper wire may be drawn to the outside so as to confirm the electrical performance of the implantable photovoltaic device. However, for the practice use of the implantable photovoltaic device, it is unnecessary to draw the copper wire to the outside. A detailed implanting process will be understood by referring to FIG. 11.

An upper picture of FIG. 2b shows a state in which the implantable photovoltaic device is placed under the skin and the skin 20 is sutured, and a lower picture of FIG. 2b shows a state in which the wound is healed after the suture.

Figure 12:
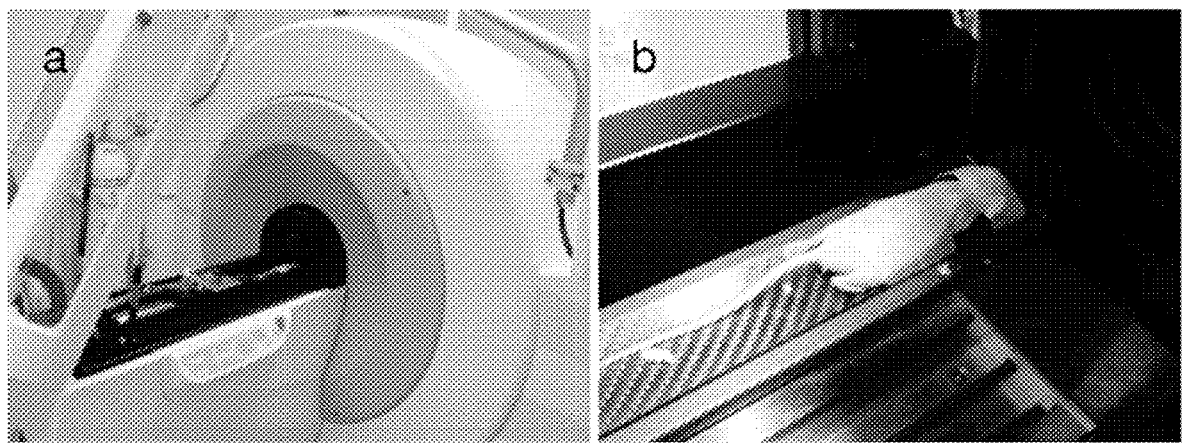

FIGS. 2c and 2d show computer tomography (CT) images in a state of being parallel to (FIG. 2c) or perpendicular to (FIG. 2d) the implantable photovoltaic device implanted into the mouse. The CT method and procedure are shown in FIG. 12.

FIG. 2e shows an image in which the implantable photovoltaic device stably mounted under the skin of the mouse is held with tweezers at the outside. It can be confirmed that the implantable photovoltaic device shows flexible characteristics like the skin.

FIG. 2f shows current-voltage characteristic curves before the implantable photovoltaic device was implanted under the skin of the mouse (dashed line) and immediately after implanted (solid line).

FIG. 2g shows the measurement result of a short circuit current density (Jsc) for four weeks after the implantable photovoltaic devices were implanted into two mice, and shows that a current (Isc) was reduced to 2.04 mA/cm$^2$ in the two mice after one week from the implant. After three weeks from the implant, the short circuit current of one mouse was slightly reduced to 1.94 mA/cm$^2$, and the short circuit current of the other mouse was slightly increased to 2.75 mA/cm$^2$. From three weeks, the short circuit currents of the two mice reached to a stable state.

Referring to FIGS. 2h to 2i, Voc (open voltage) and FF (fill factor) were almost unchanged for four weeks. Voc and FF were almost constantly maintained at 4.5 V and 0.80-0.83, respectively. The conversion efficiency showed a flow similar to Jsc (short circuit current density) of FIG. 2g. In a stabilizing step, one mouse showed the conversion efficiency of 6.9%, and the other mouse showed the conversion efficiency of 9.5%.

Meanwhile, for skin thicknesses and conversion efficiencies of the two mice into which the implantable photovoltaic devices were implanted, it is expected that the mouse having a thick skin (~675 m) will show low conversion efficiency, as compared with the mouse having a thin skin (~539).

According to the test results, it can be seen that the implantable photovoltaic device according to the embodiment can be used as a reliable in vivo power supply source for a long time.

Figure 3:
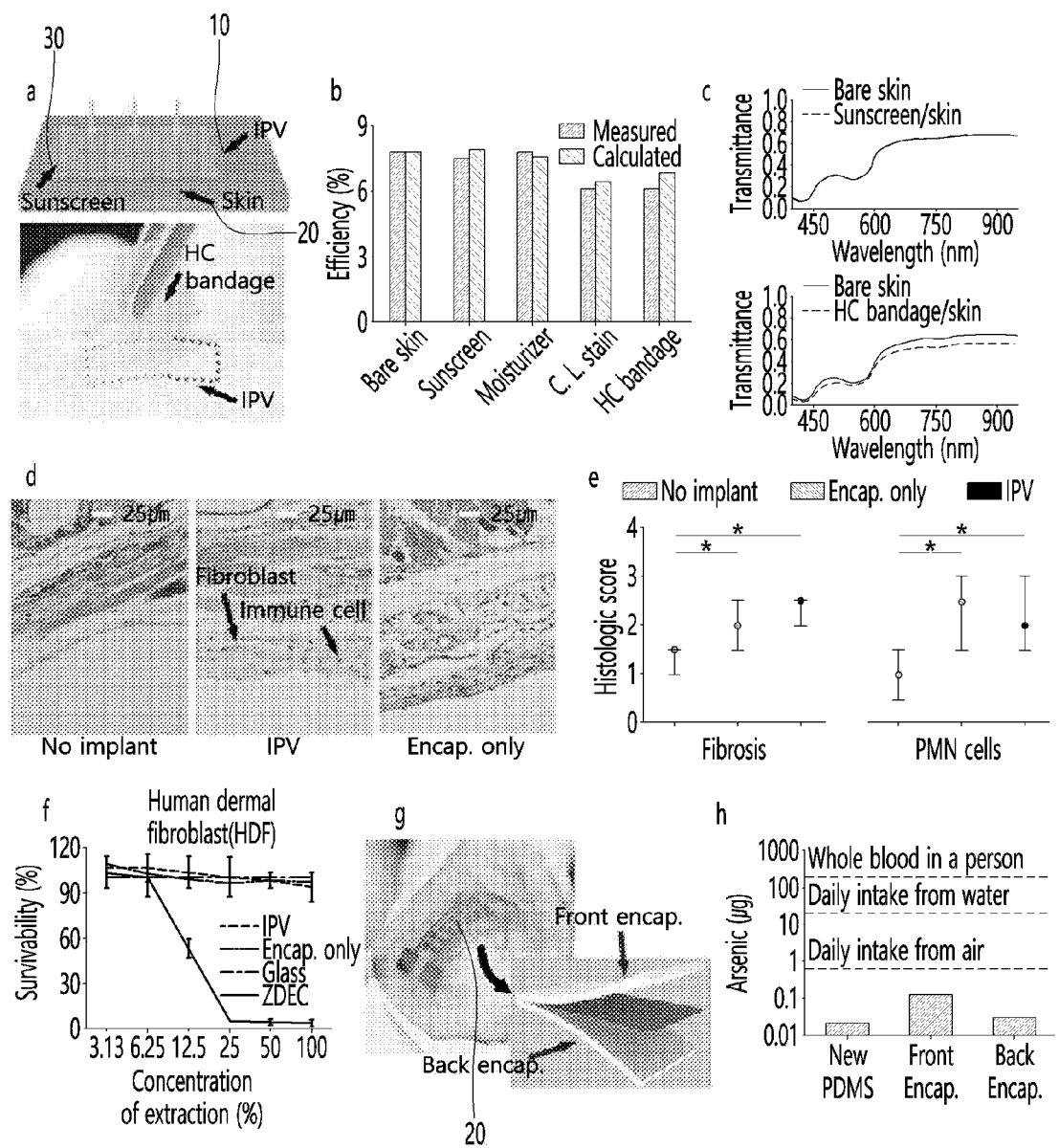

FIG. 3 is a view showing results by biocompatibility and other influences.

FIG. 3a shows an image (upper side) in which a sunscreen was applied on the skin into which the implantable photovoltaic device is implanted, and a picture (lower side) in which a hydrophilic colloid band is affixed on the skin into which the implantable photovoltaic device is implanted. The electrical characteristics of the implantable photovoltaic device were tested with respect to a case in which an additional shielding film is present on the skin into which the implantable photovoltaic device is implanted.

FIG. 3b shows measured energy conversion efficiency and calculated energy conversion efficiency when various shielding films are present on the skin into which the implantable photovoltaic device is implanted.

FIG. 3c shows skin transmittance measured when the shielding film is present on the skin. For example, it can be seen that the sunscreen for preventing sunburn has little influence on the performance of the implantable photovoltaic device according to the embodiment. This is because the sunscreen blocks ultraviolet rays having a wavelength of 280-400 nm (see Non-Patent Document 25), and thus the sunscreen has no great influence on a wavelength of 400-950 nm that the implantable photovoltaic device of the embodiment mainly absorbs. Thus, it can be seen that the solar microcells according to the embodiment preferably uses a medium for absorbing sunlight components except for ultraviolet rays harmful to the skin.

Figure 13:
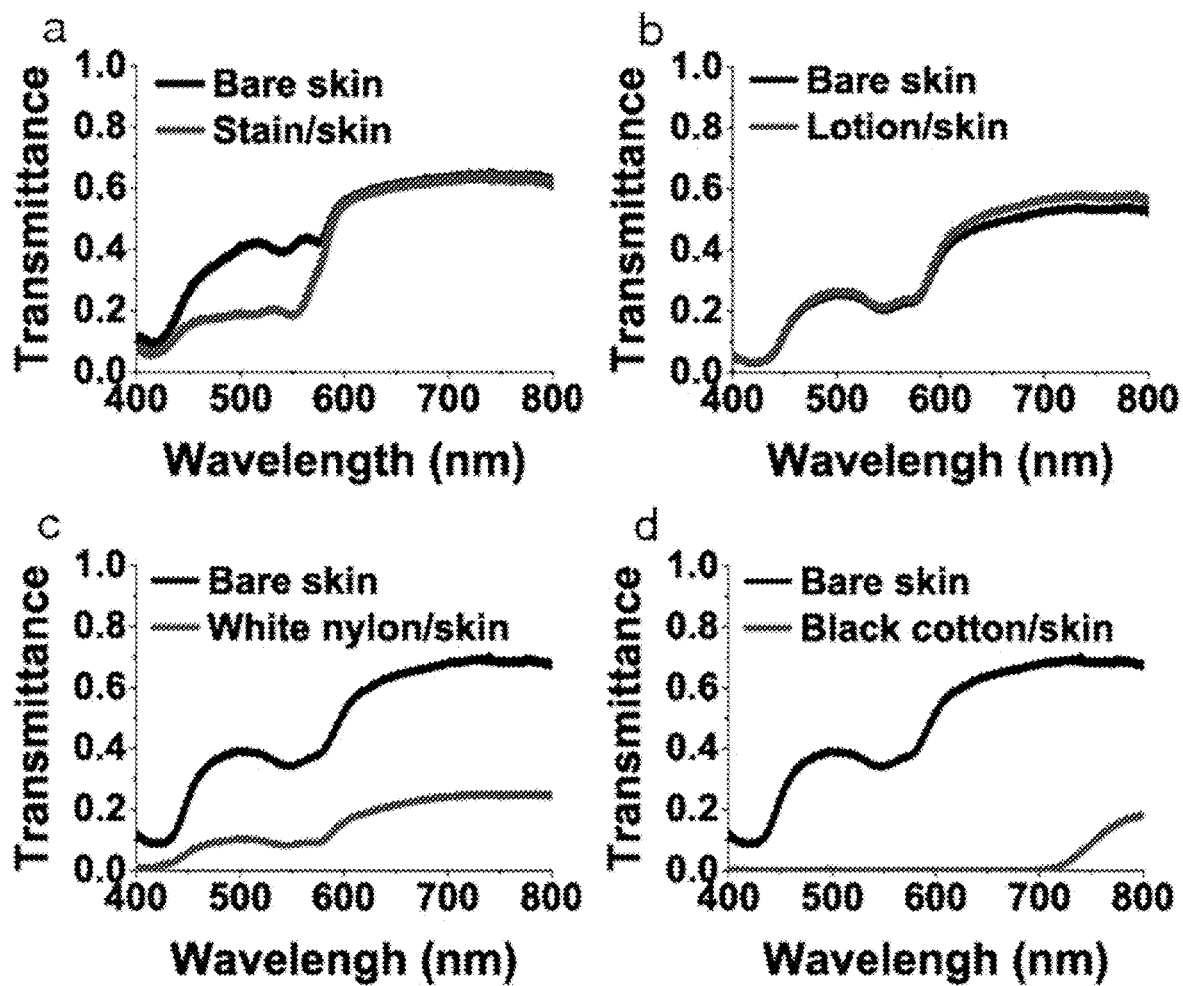

FIG. 13 is a graph showing comparison of skin transmittance between a case where the sunlight shielding film is not present on the skin and a case where various shielding films are present thereon. Table 4 shows information about various shielding films and a change in conversion efficiency due to the shielding films.

TABLE 4

| Additional layer | Ingredients | Volume or thickness | Efficency |
|---|---|---|---|
| Sunscreen | bis-ethylhexyloxyphenol methoxyphenyltriazine titanium dioxide, ethylhexylmethoxycinnamate, etc. | ~9 mg/cm$^2$ | 7.5% |
| Moisturizer | glycerin, butylene glycol, dipropylene glycol, etc. | ~13 mg/cm$^2$ | 7.8% |

TABLE 4-continued

| Additional layer | Ingredients | Volume or thickness | Efficency |
|---|---|---|---|
| Cheek-and-lip stain | ethylhexyl stearate, butylene glycol, pentylene glycol, etc. | ~5 mg/cm$^2$ | 6.1% |
| Hydrocolloid bandage | carboxymethyl cellulose, pectin, gelatin, etc. | ~0.53 mm | 6.1% |

According to the above experiment, even when a color makeup and a hydrophilic colloid band are used on the skin into which the implantable photovoltaic device is implanted, power is generated to a predetermined level by the implantable photovoltaic device according to the embodiment.

Figure 16:
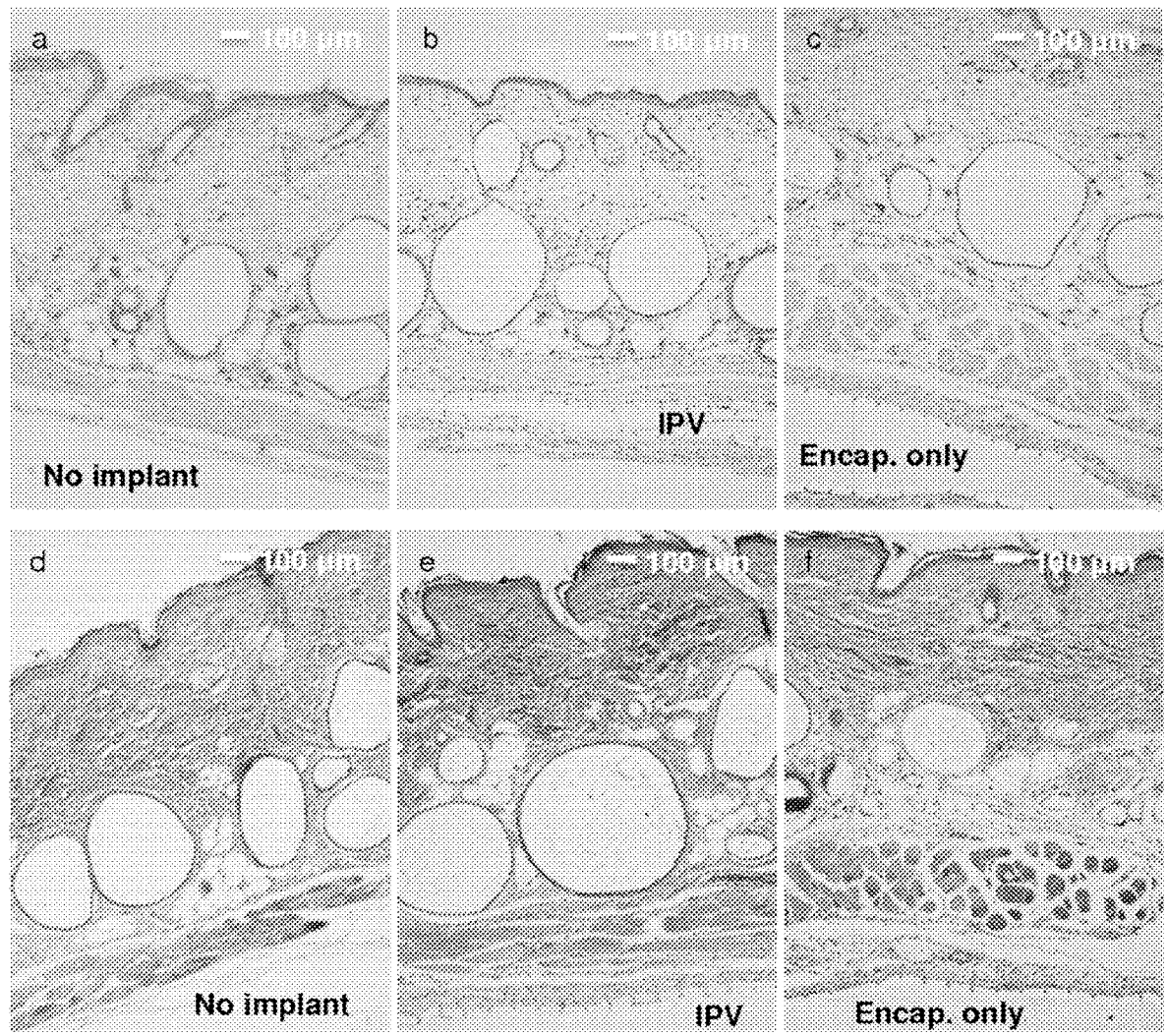

FIGS. 3d and 16 are histologic images showing comparison of skins in a case where a device from which the solar microcells 5 and the thin film wires 4 were removed (hereinafter, referred to as an encapsulation layer only), in a case where four weeks have been elapsed after the implant of the implantable photovoltaic device, and in a case where no device is implanted. The case where no device is implanted (no implant) is shown on the left side, the case of the implantable photovoltaic device (IPV) is shown in the middle, and the case where of the device consisting of the encapsulation layer only (encap. only) is shown on the right side.

Referring to FIG. 3d, it can be confirmed that there is no significant difference between the case of the implantable photovoltaic device and the case of the device consisting of the biocompatible encapsulation layer only in terms of the histologic comparison therebetween.

Figure 18:
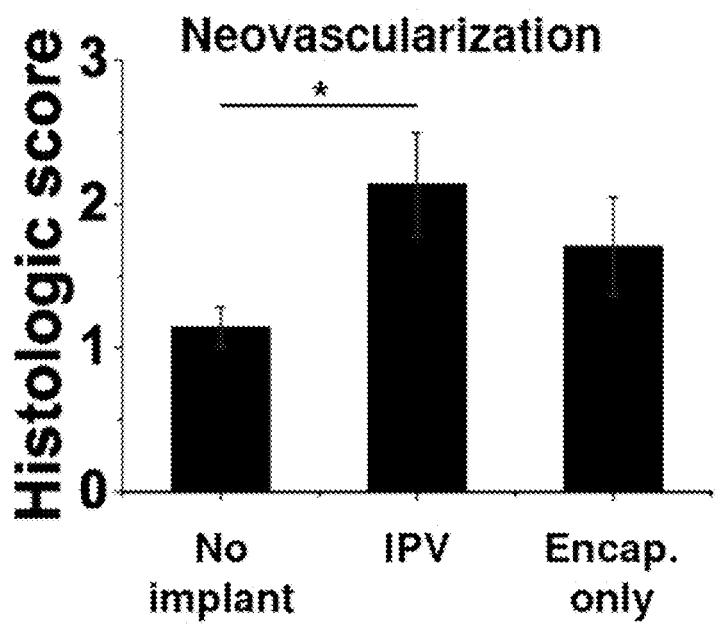

Referring to FIG. 18, even in the case of neovascularization, it can be confirmed that there is no significant difference between the case of the implantable photovoltaic device and the case of the device consisting of the biocompatible encapsulation layer only.

FIG. 3e shows a histologic scores of the degree of fibrosis and the number of polymorphonuclear cells (PWN cells) based on FIG. 3d. It can be confirmed that the histologic scores have no significant difference between the case of the implantable photovoltaic device and the case of the device consisting of the biocompatible encapsulation layer only.

Therefore, even if the implantable photovoltaic device is removed, there is no significant difference from the case where the device from which the solar microcells and the thin film wires 4 of FIG. 1a are removed from the implantable photovoltaic device, that is, the device consisting of the biocompatible encapsulation layer only is implanted, and thus it can be confirmed that there is almost no leakage of harmful components in the implantable photovoltaic device. That is, it can be seen that the device of the embodiment causes no problem in the living body.

FIG. 3f shows survivability of fibroblast after 24 hours when human dermal fibroblast (HDF) was cultured in an eluted solution in each device. The devices used in the experiment were the implantable photovoltaic device (IPV), the device (Encap. only) consisting of the biocompatible encapsulation layer only, a glass, and 0.1% zinc diethyldithiocarbamate (ZDEC) polyurethane (PU).

The survivability of the fibroblast according to the concentration of the solution extracted from the implantable photovoltaic device was very similar to those of the cases of the biocompatible glass and the device consisting of the biocompatible encapsulation layer only. On the contrary, in the case of the solution extracted from the ZDEC-PU film known as having cytotoxicity, the survivability of the fibroblast rapidly decreased from the concentration of 25% or more.

Figure 19:
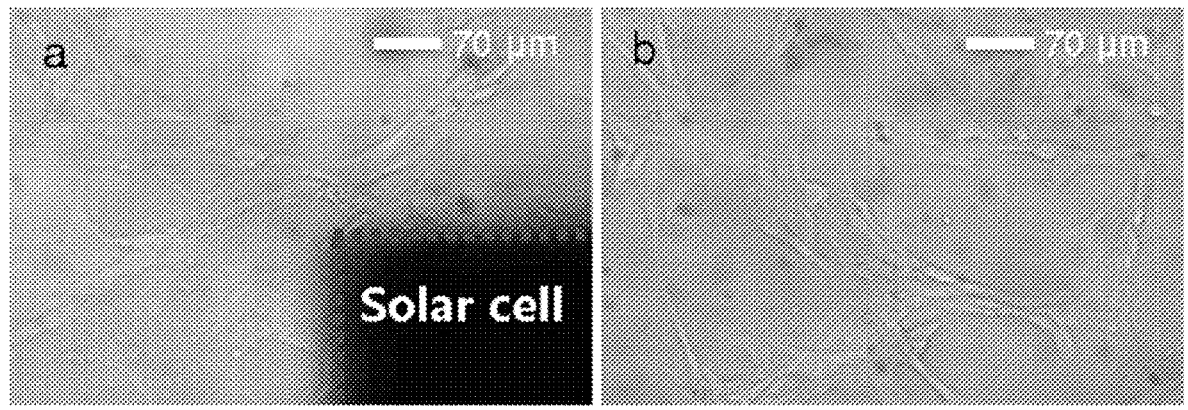

FIG. 19 clearly shows that the fibroblast was survived without problems when the fibroblast was cultured on the implantable photovoltaic device according to the embodiment.

Figure 17:
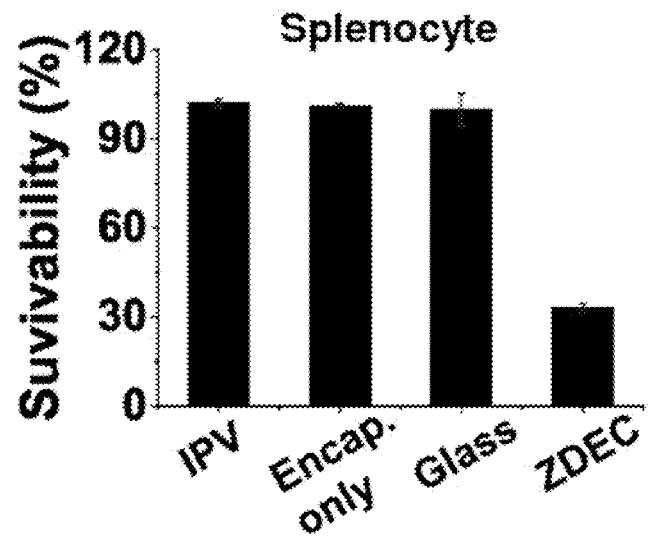

Referring to FIG. 17, when splenocyte was cultured on the implantable photovoltaic device, it was found that the survivability was almost the same as the case of the device (Encap. only) consisting of the biocompatible encapsulation layer only and a case where the splenocyte was cultured on the glass. On the contrary, it was found that the survivability of the splenocyte cultured on the ZDEC-PU film known as having cytotoxicity was very low.

Figure 20:
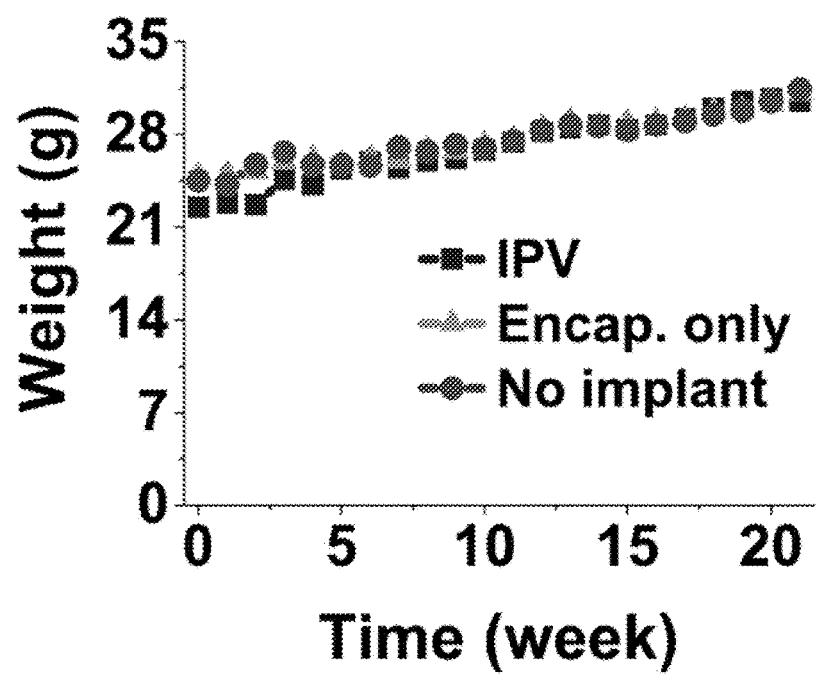

As presented in FIG. 20, it can be seen that a weight change of a mouse into which the implantable photovoltaic device was implanted was similar to a weight change of a mouse in a case where the device consisting of the biocompatible encapsulation layer only was implanted and a case where no material was implanted.

The left side of FIG. 3g shows an image of the implantable photovoltaic device stably implanted into a cellular tissue of a skin 20. It can be seen that very flexible characteristics were shown together with the skin. The right side of FIG. 3g shows a state in which a front encapsulation layer disposed at the outermost side and a back encapsulation layer were separated from the implantable photovoltaic device stably implanted under the skin.

FIG. 3h shows an amount of arsenic detected by using a resolution mass spectrometer (ICP-QMS) to analyze the front encapsulation layer disposed at the outermost side and the back encapsulation layer separated from the implantable photovoltaic device stably implanted under the skin for eight weeks as shown in the right side of FIG. 3g. Referring to the same drawing, as a result of measuring the detected arsenic amounts of a new PDMS and the encapsulation layers (size: ~7 mm×7 mm) separated from the front side and the rear side, ~0.02 g, ~0.12 g, and ~0.03 g of arsenic were respectively detected, but this is significantly smaller than the arsenic amount absorbed through water or breading by one person in a day.

Figure 4:
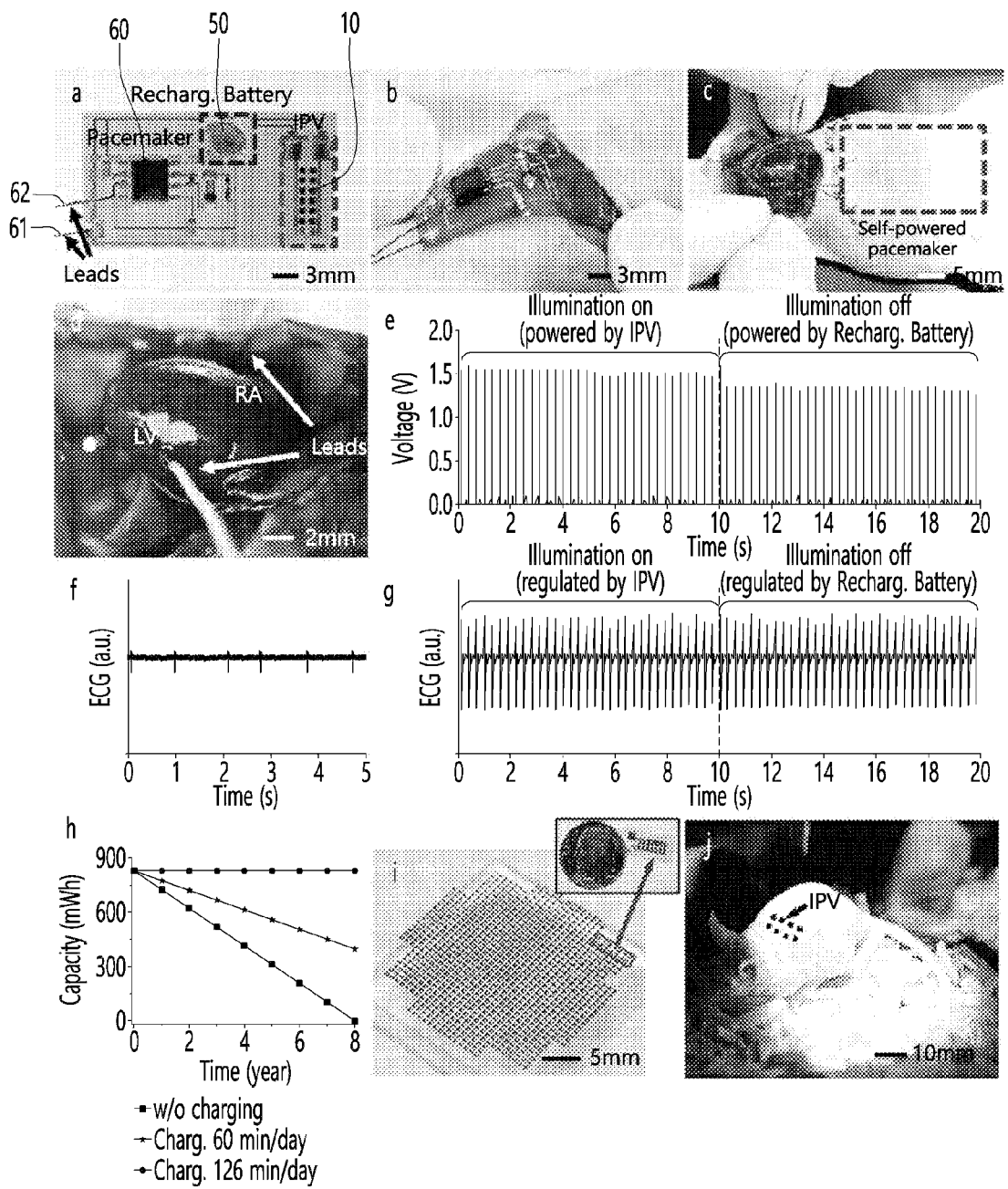

FIG. 4 shows an integrated implantable electronic apparatus to which the implantable photovoltaic device is applied.

Referring to FIG. 4a, in the implantable electronic apparatus, the implantable photovoltaic device 10, a rechargeable battery 50, and a pacemaker 60 are connected to one another. FIG. 4b shows that the device of FIG. 4a is a flexible configuration and can be implanted into the living body. FIG. 4c is a view showing that the implantable electronic apparatus according to the embodiment is implanted into the living body, and FIG. 4d shows that two lead wires 61 and 62 of the pacemaker supplied with power from the implantable photovoltaic device give electrical stimulation to a right atrium and a left ventricle of a mouse.

FIG. 4e is a view describing a 3-Hz output electric signal of the pacemaker 60. Referring to the same drawing, when the solar simulator (AM1.5G) operates, the pacemaker 60 operates with energy received from the implantable photovoltaic device (see the black drawing on the left side). At this time, a predetermined amount of energy produced by the implantable photovoltaic device 10 is stored in the rechargeable battery 50. When the solar simulator is turned off, the rechargeable battery 50 supplies energy for operating the pacemaker 60, and the pacemaker 60 generates an electric signal (see the blue drawing on the right side).

FIG. 4*f* shows an electrocardiogram of a mouse of a bradycardia state (~1 Hz), and FIG. 4*g* shows an electrocardiogram of a mouse of a bradycardia state adjusted by the pacemaker 60. Referring to the same drawing, it can be confirmed that both the case where the pacemaker 60 is operated by the implantable photovoltaic device 10 (see the black drawing on the left side) and the case where the pacemaker 10 is operated by the rechargeable battery 50 charged by the implantable photovoltaic device 10 (see the blue drawing on the right side) adjust the heart of the mouse of the bradycardia state to a targeted frequency (~3 Hz).

FIG. 4*h* shows the simulation result of the battery (Sigma 213 Lithium-Iodine, 830 mAh) used in a general pacemaker (Adapta ADDRS1, Medtronics). It can be confirmed that, when the battery is charged by the implantable photovoltaic device ($\eta$=~8.2%) for 126 minutes in a condition that the battery charging efficiency is 85%. the general pacemaker can be continuously used in a state in which the battery capacity is not consumed.

Table 3 describes the charging.

TABLE 3

Charging a pacemaker battery with the IPVs

Implantable photovoltaics
Conversion efficiency: 8.2%
Current: 160 µA
Pacemaker: Adapta ADDRS1, Medtronics
Capacity: 830 mAh (Sigma 213 lithium-iodine)
Longevity: 8 years (DDDR or DDD 50% mode)
Rate and pulse width: 60 ppm, 0.4 ms
Lead impledance: 1000 Ω
Charging efficiency: 85%
Daily power consumption
=830 mAh/(8 × 365 day) = 0.28425 mAh/day
Charging time for power consumption
=0.28425 mAh/(0.16 mA × 0.85) = 2 hr 6 min Referring to Table 3, the general pacemaker can use the battery for eight years without charging. On the contrary, in the case of the present embodiment, when the pacemaker is charged for 126 minutes or more in an ideal condition by using the implantable photovoltaic device 10, the pacemaker can be used semi-permanently without replacing the battery.

FIG. 4*i* shows a large number of solar microcells that can be manufactured, and shows that the implantable photovoltaic device 10 was manufactured by using 14 microcells. Therefore, it is shown that the size of the implantable photovoltaic device is easily adjusted so as to supply more power to the body. It can be confirmed that the implantable photovoltaic device is very small as compared with a dime of US currency which has a radius of 8.95 mm. The net area of the microcells in the implantable photovoltaic device is merely 0.07 cm². For example, since the size adjustment is easy, when the implantable photovoltaic device is manufactured by using the microcells having the net area of 0.07 cm², the pacemaker can be driven for 24 hours by Charging of about 12 minutes. FIG. 4*j* shows a relative size of the implantable photovoltaic device implanted into the mouse having few hairs.

The implantable photovoltaic device according to the embodiment can adjust the short circuit current, the open voltage, and the output power according to the energy condition required by various medical devices implanted into the living body. As a method of adjusting this, a method of changing the wiring of the thin film wire, a method of adding or removing the solar microcells, and a method of using solar microcells having different performances may be used.

The implantable photovoltaic device according to the embodiment may supply sufficient energy required for the operation of the medial device implanted into the living body, for example, the pacemaker, without additional treatments except for a simple surgical procedure.

Figure 23:
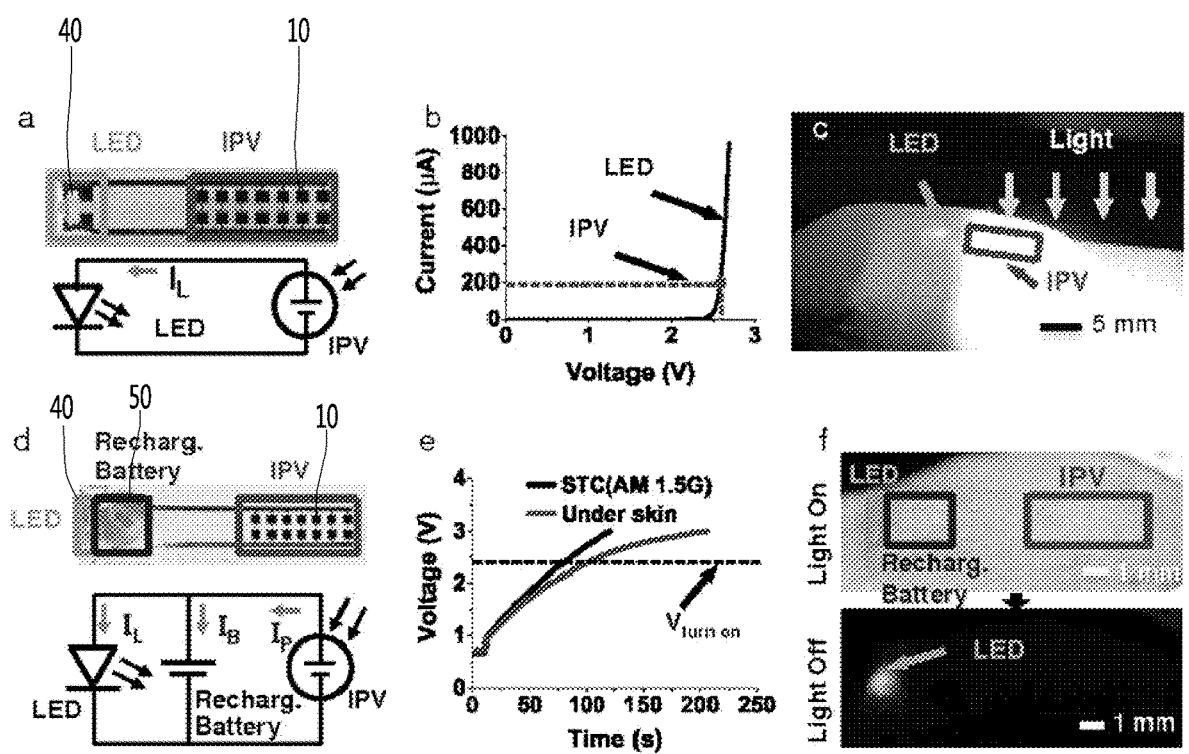

FIG. 23 shows an embodiment of another type of the implantable electronic apparatus. FIG. 23*a* shows an electronic apparatus (upper side) in which the implantable photovoltaic device 10, a rechargeable battery 50, and an electronic device (for example, LED) 40 are integrated, and an equivalent circuit thereof (lower side). FIG. 23*b* shows current-voltage characteristics of the LED. Since the open voltage (~4.5 V) of the implantable photovoltaic device is higher than the driving voltage ($V_{turn.on}$=2.4 V), it is sufficient to drive the LED. FIG. 23*c* shows that the LED emits light with power produced under the solar simulator (AM1.5G) by the implantable photovoltaic device in a state in which the implantable electronic apparatus is implanted under the skin. The malfunction of the electronic apparatus can be quickly determined by primarily determining whether the photovoltaic device implanted into the living body is normally operated by the LED. When the normal operation is confirmed, the operation of the LED is turned off through another control device, thereby preventing power waste.

FIG. 23*d* shows an image of the electronic apparatus integrated with the LED 40, the rechargeable battery 50, and the implantable photovoltaic device 10 (upper side) and an equivalent circuit thereof (lower side). A current (Ip) generated by the implantable photovoltaic device 10 can drive the LED 40 (IL) and can recharge the battery 50 (IB).

FIG. 23*e* shows the charging time of the battery by the implantable photovoltaic device and shows a standard test condition (STC, AM1.5G, black solid line) and a state of being implanted into the skin of the mouse (red solid line). According to this, as compared with the case of being placed in the outside, when implanted under the skin, the driving time and the charging time of the LED 400 are slightly longer.

In FIG. 23*f*, the integrated electronic device completely implanted under the skin of the mouse turns on the LED under the solar simulator and stores energy in the rechargeable battery. When there is no illumination, the LED can be enabled to emit light by supplying the energy to the LED by using the energy stored in the battery.

FIG. 24 is a view describing the configuration of the implantable electronic apparatus and the operation state of the rechargeable battery.

Specifically, FIG. 24*a* shows a circuit diagram of the implantable photovoltaic device 10 and the rechargeable battery 50, and shows a charging voltage curve (left) and an equivalent circuit (right) when the solar simulator is turned on and off. Although a predetermined voltage drop occurs due to an internal resistance of the battery, it can be confirmed that the rechargeable battery 50 is charged by the implantable photovoltaic device 10 placed under the skin of the mouse having few hairs.

FIG. 24*b* is a charging/discharging voltage curve (left) and an equivalent circuit (right) of the rechargeable battery 50 according to the on/off of the solar simulator when the implantable photovoltaic device 10 connected to the LED 40 and the rechargeable battery 50 presented in FIG. 23*d* is placed under the skin of the mouse having few hairs. When the solar simulator is turned off, the rechargeable battery 50 supplies power to the LED, and thus the voltage of the rechargeable battery 50 is reduced.

FIG. 24*c* is a charging/discharging voltage curve (left) and an equivalent circuit (right) of the rechargeable battery 50 according to the on/off of the solar simulator when the implantable photovoltaic device 10 connected to the rechargeable battery 50 and the pacemaker 60 presented in FIG. 4a is placed under the skin of the mouse having few hairs. When the solar simulator is turned off, the rechargeable battery 50 supplies power to the pacemaker, and thus the voltage of the rechargeable battery 50 is reduced.

Figure 5:
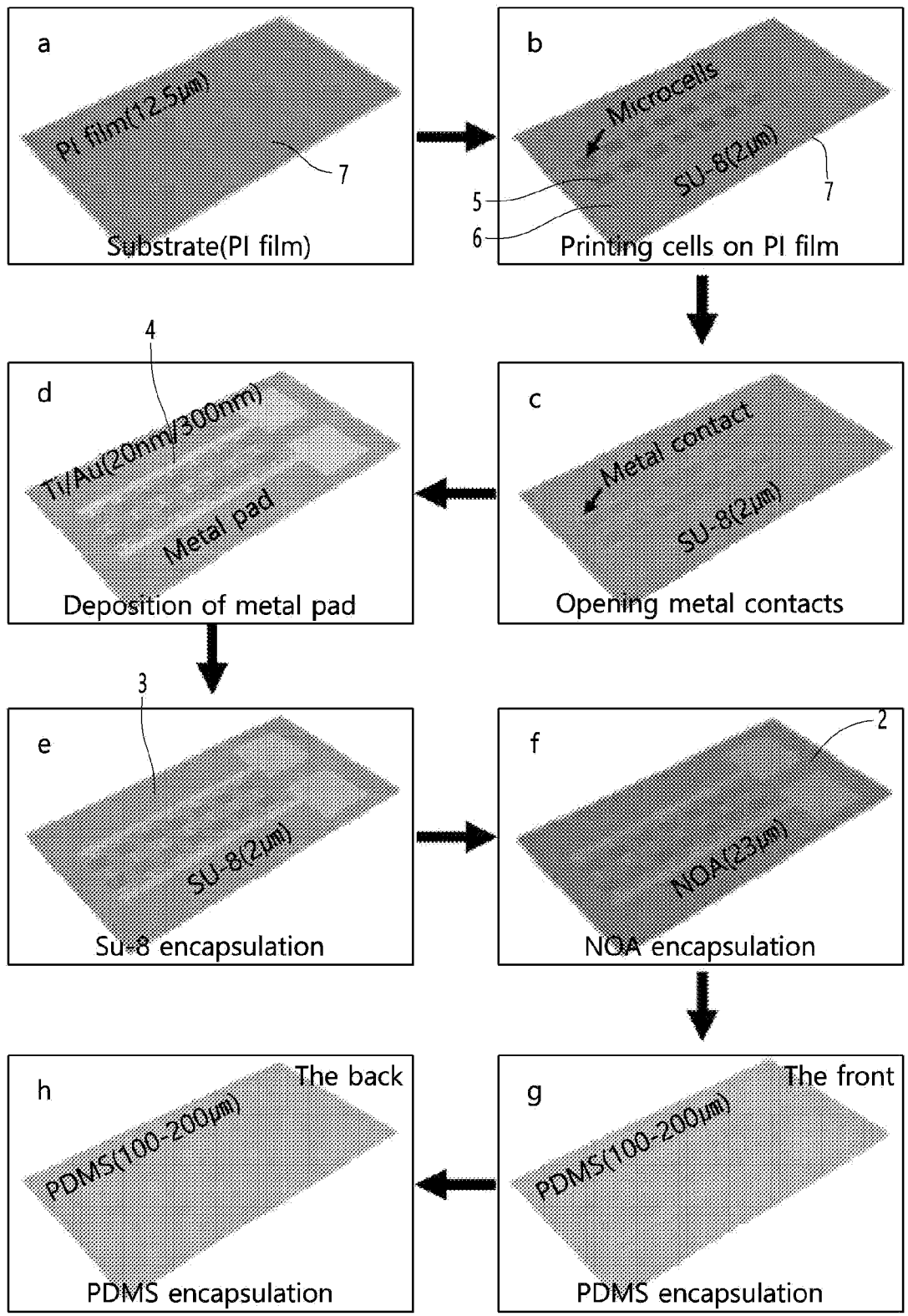

FIG. 5 is a view describing a method of manufacturing an implantable photovoltaic device according to an embodiment. The configuration of the implantable photovoltaic device will be described in more detail.

Referring to FIG. 5, dual-junction solar microcells 5 are manufactured on a substrate (wafer). At this time, an electrode may be provided to each of the solar microcells 5. Specifically, a method introduced in Non-Patent Document 29 and the like may be used.

By using a PDMS stamp (sacrificial stamp), the solar microcells 5 are detached from the substrate on which the solar microcells are manufactured. Subsequently, the solar microcells 5 are transferred onto a transfer film 7 shown in FIG. 5a (PI film may be used) (see FIG. 5b). At this time, in order to increase transfer efficiency, an adhesive layer 6 (SU-8 may be used) may be previously coated on the transfer film to a predetermined thickness before the solar microcells 5 are transferred.

The solar microcells may be attached to the transfer film without the adhesive layer. As the method thereof, cold welding may be used. As for the cold welding, the solar microcells and the transfer film are attached to each other by applying heat and pressure in a state in which the PDMS stamp having the solar microcells attached thereto is attached to the transfer film, and then, the PDMS stamp is detached therefrom.

Of the two attaching method, the case where the adhesive layer is provided is preferable so as to increase transfer efficiency. However, when the adhesive layer is present, heat dissipation does not occur and the device becomes thick.

Subsequently, upper and lower electrode surfaces of the solar microcells are exposed so that thin film wires 4 connecting the solar microcells 5 are stacked (FIG. 5c). Subsequently, the thin film wires 4 are deposited (FIG. 5d). The method of depositing the thin film wires may use sputtering.

The thin film wires 4 may be protected by an encapsulation layer made of an optically transparent material having biocompatibility.

The encapsulation layer includes an upper encapsulation layer protecting the upper side of the solar microcell. Specifically, as the upper encapsulation layer, a first layer 3 using SU-8 is first coated (FIG. 5e), and a second layer 2 using Norland optical adhesives (NOA) is additionally coated (FIG. 5f). An encapsulation layer of a third layer 1 may be stacked on the second layer by using PDMS (FIG. 5g). The first layer may be provided to be thinner than the second layer. The second layer may be provided to be thinner than the third layer. It is a main object to prevent excessive strain from being applied to the solar microcells and the thin film wires.

Finally, the lower surface of the transfer film 7 is protected by the lower encapsulation layer 8 by using PDMS having been used in the third layer (see FIG. 5h). The upper encapsulation layer and the lower encapsulation layer may be connected to each other, so that the solar microcells and the thin film wires are sealed from the outside. Therefore, the solar microcells and the thin film wires including harmful metal materials or the like may not affect the living body.

Meanwhile, the LED, the battery, and the like may be connected on the thin film wires 4 by using a conductive epoxy layer before the solar microcells 5 and the thin film wires 4 are encapsulated by the encapsulation layers 1, 2, 3, 6, 7, and 8.

FIG. 6 is a cross-sectional view of a manufactured implantable photovoltaic device. A specific configuration can be confirmed in more detail with reference to the cross-sectional view.

FIG. 6a shows that, considering the elastic modulus and the thickness of each material constituting the encapsulation layers, it is preferable that a central position of a variation (a neutral plane for deformation) when a bending motion occurs (in a vertical direction when viewed from the ground) passes through the microcells.

In addition, the outer layer among the multilayers constituting the encapsulation layer may use a material having a small elastic modulus, as compared with the inner layer. The reason is that the outer layer is allowed to be easily deformed like the skin, so as to reduce physical adverse effects on the cells and tissues of the skin when the implantable photovoltaic device is implanted. Another reason is that the inner layer is provided with a material having a high elastic modulus, so as to reduce adverse effects (damage) on the solar microcells or the thin film wires and reduce the thickness of the implantable photovoltaic device.

Meanwhile, the outer layer has the same physical characteristics as those of the skin as far as possible, so as to prevent deformation affecting the skin and damage to the device.

The mathematical calculation of the neural plane is shown in Table 1.

TABLE 1

$E_{SU} = 2$ Gpa, $E_{pl} = 3.2$ Gpa
$E_{noa} = $ Gpa, $E_{pd} = 2$ Mpa
$H_{pl} = 12.5$ μm, $H_{tpd} = H_{bpd} = 100$ μm,
$H_{TRL} = 10$ μm, $H_{hz1} = 2$ μm, $H_{noa} = 23$ μm
$L = 7.5$ mm, $L_{pl} = E_{pl}/E_{pd} \times L$,
$L_{SU} = E_{SU}/E_{DS} \times L$, $L_{noa} = E_{noa}/E_{pd} \times L$
$S_1 = H_{apd}/2$, $S_2 = H_{pd} + H_{pl}/2$, $S_3 = H_{pd} + H_{pd} + (H_{DsU} + H_{Du})/2$
$S_4 = H_{pd} + H_{pl} + H_{bsU} + H_{LsU} + H_{noa}/2$
$S_5 = H_{pd} + H_{pl} + H_{bsU} + H_{bu} + H_{noa} + H_{tpd}/2$
$A_1 = L \times H_{tpd}$, $A_2 = L_{pl} \times H_{pl}$, $A_3 = L_{su} \times H_{su}$,
$A_4 = L_{noa} \times E_{nos} A_5 = L_{tpd} \times H_{tpd}$
$S_{neutral\ plane} = \Sigma S_i A_i / \Sigma A_i$,
$S_{neutral\ plane} = (S_1 A_1 + S_2 A_2 + S_3 A_3 + S_4 A_4 + S_5 A_5)/(A_1 + A_2 + A_3 + A_4 + A_5)$
$S_{neutral\ plane} = 117.5$ μm(center of microcells)

Figure 7:
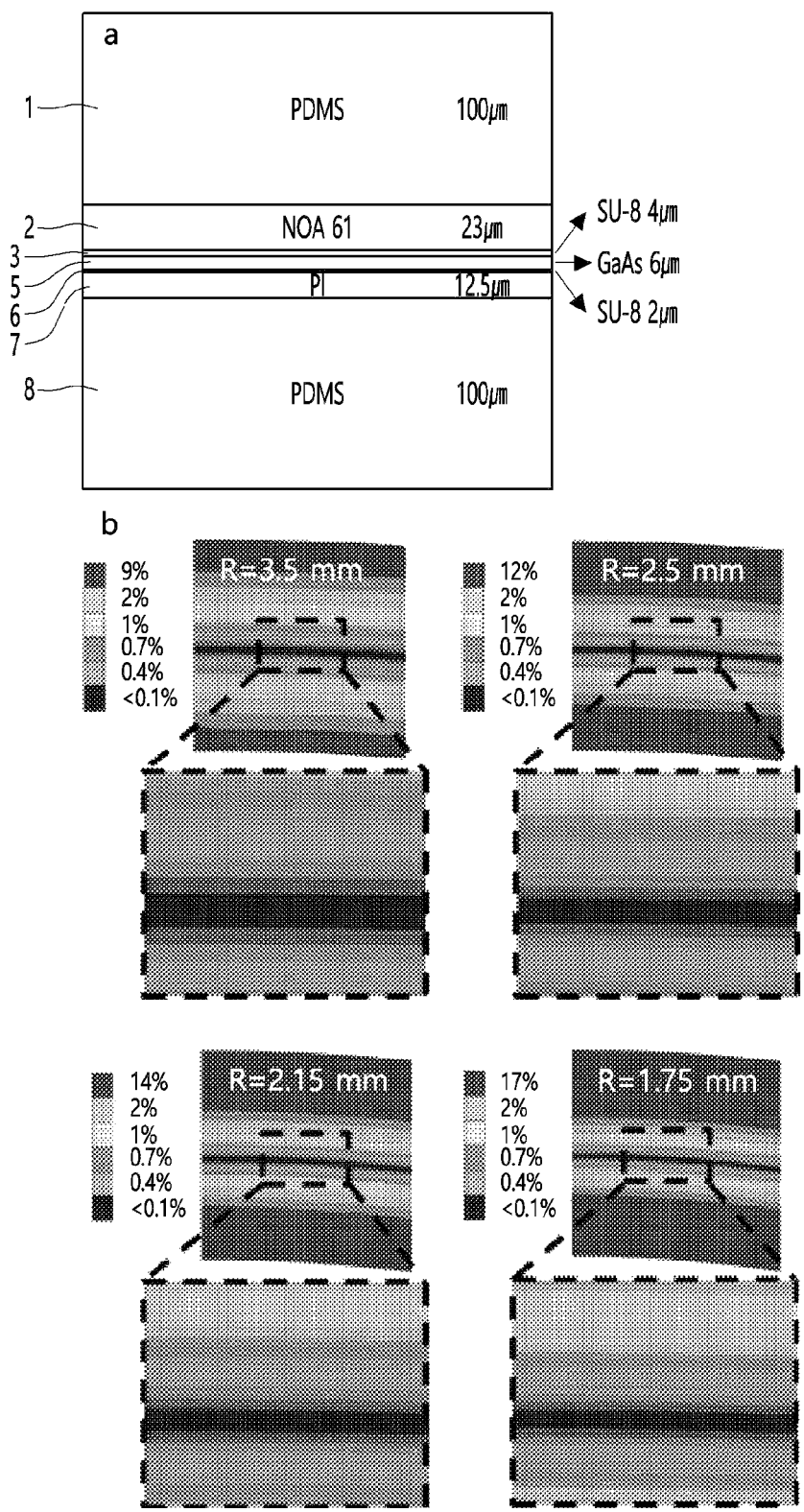

FIG. 7 shows a calculation of a deformation rate applied to the solar microcells by using a finite element method when bending (1.75 to 3.5 mm) of various radius curvatures is applied to the implantable photovoltaic device. It can be confirmed that the strain rate is merely about 0.1%. This is because the position of the solar microcell is located on the neutral plane with respect to the deformation. In addition, even if there is such deformation, it is a deformation acceptable by the encapsulation layer, and the deformation rate occurring in the solar microcells or the thin film wires may be a negligible value.

FIG. 15 is a view showing a change in the conversion efficiency of the implantable photovoltaic device implanted under the skin when an incident angle of light is changed, and shows that the conversion efficiency is lowered according to an incident direction of light, and thus light is incident in a direction perpendicular to the skin as much as possible.

INDUSTRIAL APPLICABILITY

According to the present invention, electricity can be semi-permanently obtained in the living body without a complicated medical procedure. Therefore, the bio-implantable medical device can be used without repeated operations for battery replacement and periodic recharging.

The invention claimed is:

1. An implantable photovoltaic device using absorption of light penetrating a skin, the implantable photovoltaic device comprising:
    at least two solar microcells configured to absorb sunlight;
    a thin film wire configured to connect the at least two solar microcells to each other;
    a film configured to support the solar microcells; and
    an encapsulation layer including an upper encapsulation layer configured to encapsulate an upper side of the solar microcells and shield the solar microcells, and
    a lower encapsulation layer configured to encapsulate a lower side of the film and connect to the upper encapsulation layer,
    wherein the upper encapsulation layer includes multilayers,
    wherein an outer layer among the multilayers comprises a material having a smaller elastic modulus than an inner layer among the multilayers, and
    wherein the inner layer among the multilayers is thinner than the outer layer among the multilayers.

2. The implantable photovoltaic device according to claim 1, further comprising an adhesive layer configured to adhering the film and the at least two solar microcells to each other.

3. The implantable photovoltaic device according to claim 2, wherein the adhesive layer is SU-8.

4. The implantable photovoltaic device according to claim 1, wherein the upper encapsulation layer comprises:
    a first layer coated on the upper side of the solar microcells;
    a second layer on the first layer; and
    a third layer on the second layer, and
    the first layer is thinner than the second layer, and the second layer is thinner than the third layer.

5. The implantable photovoltaic device according to claim 4, further comprising an adhesive layer configured to adhere the film and the at least two solar microcells to each other,
    wherein the first layer includes the same material as the adhesive layer.

6. The implantable photovoltaic device according to claim 4, wherein the second layer is NOA, and the third layer is PDMS.

7. The implantable photovoltaic device according to claim 1, wherein the upper encapsulation layer comprises:
    a first layer coated on the upper side of the solar microcells;
    a second layer on the first layer; and
    a third layer on the second layer, and
    the first layer has a smaller elastic modulus than the second layer, and the second layer has a larger elastic modulus than the third layer.

8. The implantable photovoltaic device according to claim 1, wherein the lower encapsulation layer is made of PDMS.

9. The implantable photovoltaic device according to claim 1, wherein the film is a PI film.

10. The implantable photovoltaic device according to claim 9, wherein the solar microcells are transferred onto the PI film.

11. The implantable photovoltaic device according to claim 1, wherein the solar microcells are arranged with two rows and seven columns.

12. The implantable photovoltaic device according to claim 1, wherein a neutral plane for deformation by a bending motion of the implantable photovoltaic device passes through the at least two solar microcells.

13. An electronic apparatus used for supplying power to the inside of a living body, the electronic apparatus comprising:
    a photovoltaic device comprising:
        at least two solar microcells configured to absorb sunlight;
        a thin film wire configured to connect the at least two solar microcells to each other;
        a film configured to support the solar microcells;
        an encapsulation layer including an upper encapsulation layer configured to encapsulate an upper side of the solar microcells and shield the solar microcells,
        a lower encapsulation layer configured to encapsulate a lower side of the film and connect to the upper encapsulation layer; and
        a battery configured to store electricity produced by the photovoltaic device,
    wherein the upper encapsulation layer includes multilayers,
    wherein an outer layer among the multilayers comprises a material having a smaller elastic modulus than an inner layer among the multilayers, and
    wherein the inner layer among the multilayers is thinner than the outer layer among the multilayers.

14. The electronic apparatus according to claim 13, wherein the electronic- apparatus comprises an electronic element connected to at least the battery.

15. The electronic apparatus according to claim 14, wherein the electronic element comprises a pacemaker or an LED.

16. The electronic apparatus according to claim 13, wherein the photovoltaic device is configured to be placed at a neck.

* * * * *